(12) United States Patent
Stern et al.

(10) Patent No.: US 11,612,322 B2
(45) Date of Patent: Mar. 28, 2023

(54) SEARCHING SYSTEM FOR BIOSIGNATURE EXTRACTION AND BIOMARKER DISCOVERY

(71) Applicant: THE BRIGHAM AND WOMEN'S HOSPITAL, INC., Boston, MA (US)

(72) Inventors: Emily Stern, Chestnut Hill, MA (US); David Silbersweig, Chestnut Hill, MA (US); Hong Pan, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 357 days.

(21) Appl. No.: 16/753,020

(22) PCT Filed: Oct. 3, 2018

(86) PCT No.: PCT/US2018/054218
§ 371 (c)(1),
(2) Date: Apr. 2, 2020

(87) PCT Pub. No.: WO2019/070887
PCT Pub. Date: Apr. 11, 2019

(65) Prior Publication Data
US 2020/0288980 A1    Sep. 17, 2020

Related U.S. Application Data

(60) Provisional application No. 62/567,608, filed on Oct. 3, 2017.

(51) Int. Cl.
*A61B 5/00*     (2006.01)
*G16H 70/60*    (2018.01)
(Continued)

(52) U.S. Cl.
CPC ............ *A61B 5/0042* (2013.01); *A61B 5/055* (2013.01); *A61B 5/16* (2013.01); *G01R 33/4806* (2013.01);
(Continued)

(58) Field of Classification Search
CPC ......... A61B 5/0042; A61B 5/055; A61B 5/16; A61B 5/4884; A61B 2576/026;
(Continued)

(56) References Cited

U.S. PATENT DOCUMENTS 9,773,308 B2    9/2017  Silbersweig
2002/0082495 A1  6/2002  Biswal
(Continued)

FOREIGN PATENT DOCUMENTS

WO    WO-0139664 A1 * 6/2001  ........... A61B 5/0484
WO    2015066679 A2    5/2015

OTHER PUBLICATIONS

International Searching Authority, International Search Report and Written Opinion for application PCT/US2018/054218, dated Dec. 6, 2018.

(Continued)

*Primary Examiner* — Susan S Lee
(74) *Attorney, Agent, or Firm* — Quarles & Brady LLP

(57) ABSTRACT

An automated system and method is provided for biotype extraction and biomarker discovery from task-based fMRI imaging data. The system and method may include automatically mapping a localizome, such as a task-condition/contrast/population-specific brain functional localizome, based on fMRI data and automatically selecting and sorting brain regions or brain nodes to produce a subset of functional brain regions or brain nodes. A report may then be generated indicating that the subject has a particular brain circuit pattern of activity and connectivity associated with (Continued)

one or more symptoms of the given mental disorder, treatments, or associated with normal brain functions, based upon the extracted biosignatures by searching for the optimal multivariate classifier with least dimensionality in the brain functional localizome. These biosignatures and biomarkers that reveal hidden, implicit, and latent brain circuit patterns provoked by fMRI tasks, can also provide for the development of non-invasive diagnostics and targeted therapeutics in neuropsychiatric diseases.

22 Claims, 18 Drawing Sheets

(51) Int. Cl.
| | | |
|---|---|---|
| G16H 15/00 | (2018.01) | |
| G16H 50/30 | (2018.01) | |
| G16H 50/70 | (2018.01) | |
| G16H 50/20 | (2018.01) | |
| G16H 30/40 | (2018.01) | |
| A61B 5/055 | (2006.01) | |
| A61B 5/16 | (2006.01) | |
| G01R 33/48 | (2006.01) | |
| G01R 33/56 | (2006.01) | |
| G06T 7/00 | (2017.01) | |

(52) U.S. Cl.
CPC ........ *G01R 33/5608* (2013.01); *G06T 7/0012* (2013.01); *G16H 15/00* (2018.01); *G16H 30/40* (2018.01); *G16H 50/20* (2018.01); *G16H 50/30* (2018.01); *G16H 50/70* (2018.01); *G16H 70/60* (2018.01); *A61B 5/4884* (2013.01); *A61B 2576/026* (2013.01); *G06T 2207/10088* (2013.01); *G06T 2207/30016* (2013.01)

(58) Field of Classification Search
CPC  A61B 5/4088; A61B 5/4064; G01R 33/4806; G01R 33/5608; G06T 7/0012; G06T 2207/10088; G06T 2207/30016; G16H 15/00; G16H 30/40; G16H 50/20; G16H 50/30; G16H 50/70; G16H 70/60; G06K 9/0057
See application file for complete search history.

(56) References Cited

U.S. PATENT DOCUMENTS

| | | |
|---|---|---|
| 2016/0019693 A1 | 1/2016 | Silbersweig |
| 2016/0025828 A1 | 1/2016 | Jiang et al. |
| 2016/0300352 A1 | 10/2016 | Raj |

OTHER PUBLICATIONS

European Patent Office. Extended European Search Report for application 18865255.6, dated Apr. 30, 2021. 8 pages.

* cited by examiner

SEARCHING SYSTEM FOR BIOSIGNATURE EXTRACTION AND BIOMARKER DISCOVERY

CROSS-REFERENCE TO RELATED APPLICATIONS

This application represents the U.S. National Stage Entry of International Application PCT/US2018/054218, filed Oct. 3, 2018, which is based on, claims the benefit of, and claims priority to U.S. Provisional Application 62/567,608, filed Oct. 3, 2017. Each of the preceding applications is hereby incorporated herein by reference in its entirety for all purposes.

STATEMENT OF FEDERALLY SPONSORED RESEARCH OR DEVELOPMENT

This invention was made with government support under R01 ME161825 and P50 ME158911 awarded by the National Institutes of Health. The government has certain rights in the invention.

BACKGROUND

Task-based fMRI studies result in an abundance of information that is not available via other imaging modalities, including resting-state fMRI. Task-based studies are able to perturb resting brain states to assess the function of the multiple brain circuits that are active in response to specific external stimuli. This "stress test" for the brain can be tailored to probe particular brain structures/circuits and their related functions, or can be used more comprehensively to assess function across the entire brain in response to the administered stimuli.

SUMMARY OF THE DISCLOSURE

The present disclosure provides a system and method for biosignature extraction and biomarker discovery from task-based fMRI imaging data. In some configurations, the method may reveal hidden, implicit, and latent brain circuit patterns provoked by fMRI tasks.

In one configuration, a computer-implemented method is provided for extracting biosignatures for an individual subject having a given mental disorder. In some configurations, the mental disorder may be previously descriptively or subjectively defined by The Diagnostic and Statistical Manual of Mental Disorders, Fifth Edition (DSM-5) or an individual healthy control subject. The method includes receiving, at a processor, task-based functional magnetic resonance imaging (fMRI) data for the individual subject and one or more populations. The method may then include automatically mapping, using the processor, a localizome, such as a task-condition/contrast-specific brain functional localizome based on the fMRI data and automatically selecting and sorting brain regions or brain nodes, using the processor and the localizome to produce a functional subset of brain regions or brain nodes. A multivariate classifier indicating that the subject has particular brain circuit patterns of activity and connectivity associated with one or more symptoms or treatments of the given mental disorder or associated with normal brain functions, may be produced by automatically searching the optimal parameter space of the classifier over the most parsimonious supporting space of brain functional localizome using the processor, and resulted in the functional subset of brain regions or brain nodes that reveal all the salient aspects of the brain "stress test". A report may then be generated providing the objective explanation based on neurobiological mechanism of one or more symptoms the subject has that are associated with the given mental disorder, which may be previously subjectively or descriptively defined by DSM-5 or associated with normal brain functions.

In one configuration, an fMRI system is provided. The system includes a magnet system configured to generate a polarizing magnetic field about at least a portion of a subject arranged in the fMRI system. The system also includes a magnetic gradient system including a plurality of magnetic gradient coils configured to apply at least one magnetic gradient field to the polarizing magnetic field and a radio frequency (RF) system configured to apply an RF field to the subject and to receive fMRI signals therefrom. The system also includes a computer system programmed to: control the fMRI system to acquire task-based fMRI data for an individual subject having a given mental disorder (the mental disorder may be previously subjectively defined by DSM-5 or an individual healthy control subject); acquire fMRI data for one or more populations; map a localizome, such as a task-condition/contrast/population-specific brain functional localizome, based on the fMRI data for the individual subject having the given mental disorder or treatment; select and sort brain regions or brain nodes using the localizome to produce a functional subset of brain regions or brain nodes of the individual subject; search the optimal parameter space of the classifier over the most parsimonious supporting space of brain functional localizome to produce an optimal multivariate classifier indicating that the subject has particular brain circuit patterns of activity and connectivity associated with one or more symptoms or treatments of the given mental disorder or associated with normal brain functions; and generate a report providing the objective explanation based on neurobiological mechanism of one or more symptoms or treatments the subject has that are associated with the given mental disorder, which may be previously subjectively or descriptively defined by DSM-5 or associated with normal brain functions.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

Figure 5A:
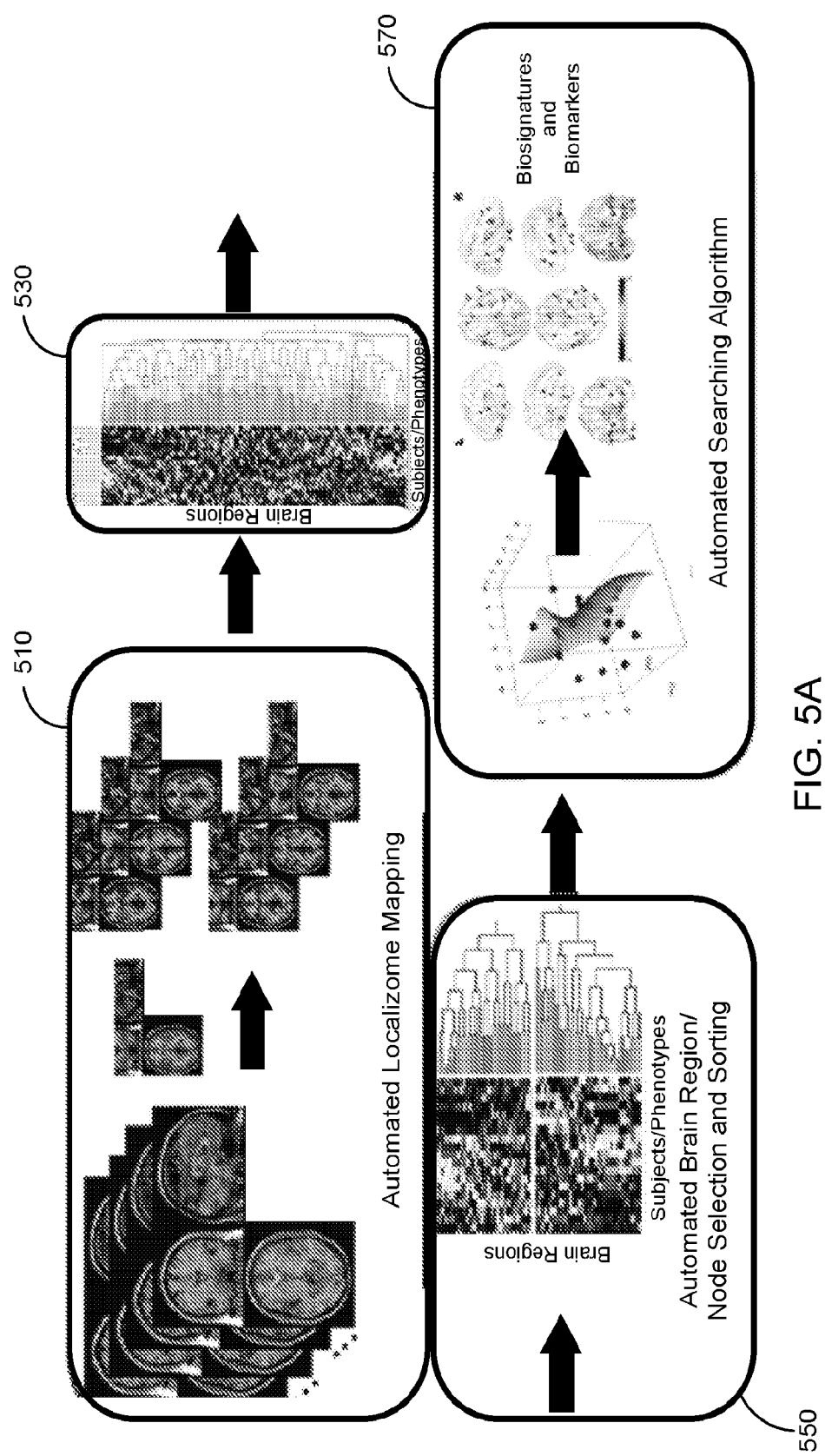
FIG. 5A is a diagram that summarizes one non-limiting example of a multivariate, automated, systematic and hierarchical searching algorithm for objective biosignature extractions within/between/among 1 or 2 or more than 2 populations of mental disorders and/or healthy controls according to an embodiment of the invention.
Figure 5B:
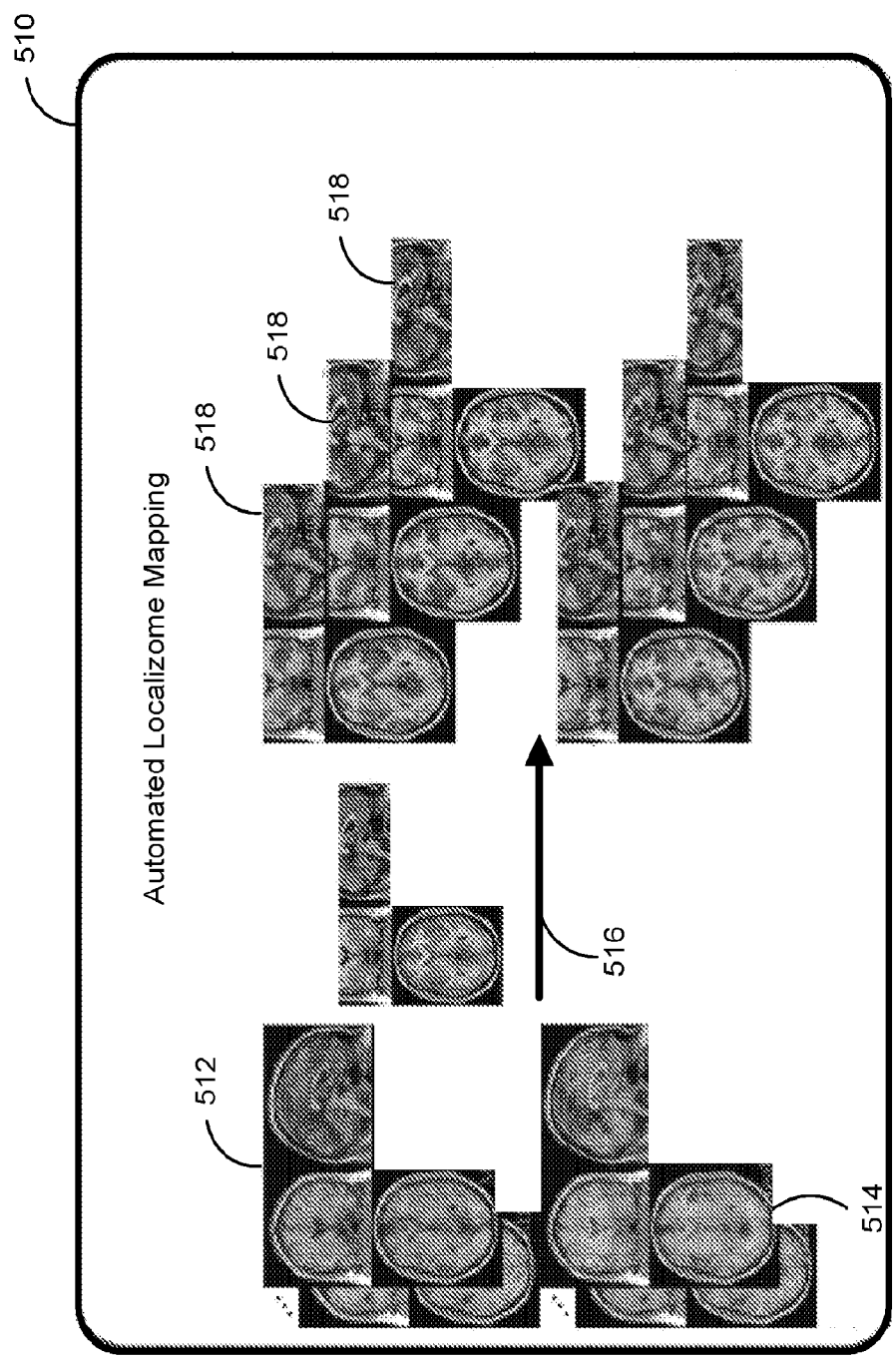

FIG. 5B is a diagram that shows one non-limiting example of an automated localizome, such as a task-condition/contrast/population-specific brain functional localizome, mapping algorithm based on task-based fMRI data utilizing a normalized spectral clustering method at a population level.

Figure 5C:
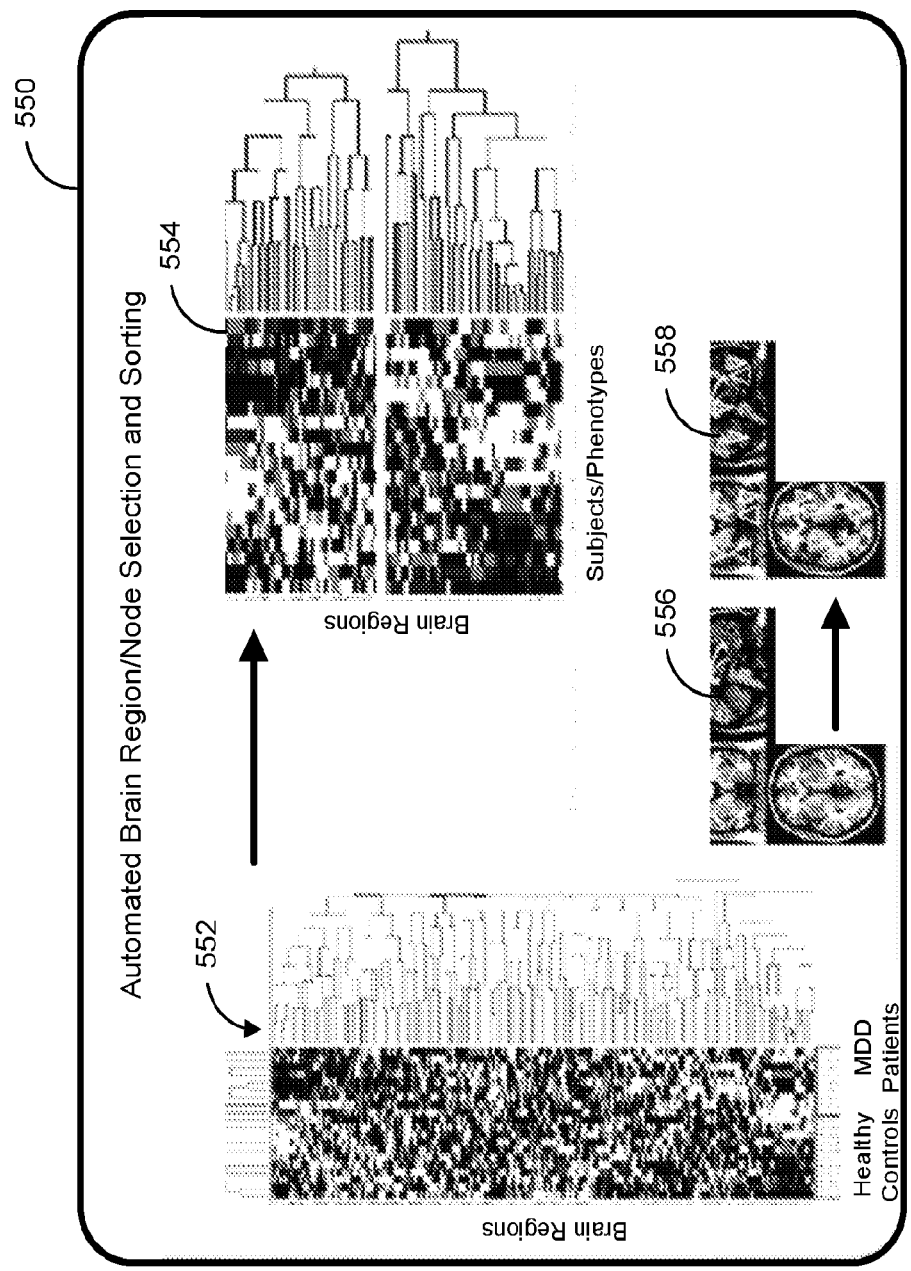

FIG. 5C is a diagram that shows one non-limiting example of an automated brain region/node selection and sorting algorithm utilizing an unsupervised two-way hierarchical clustering analysis method at the population level.

Figure 5D:
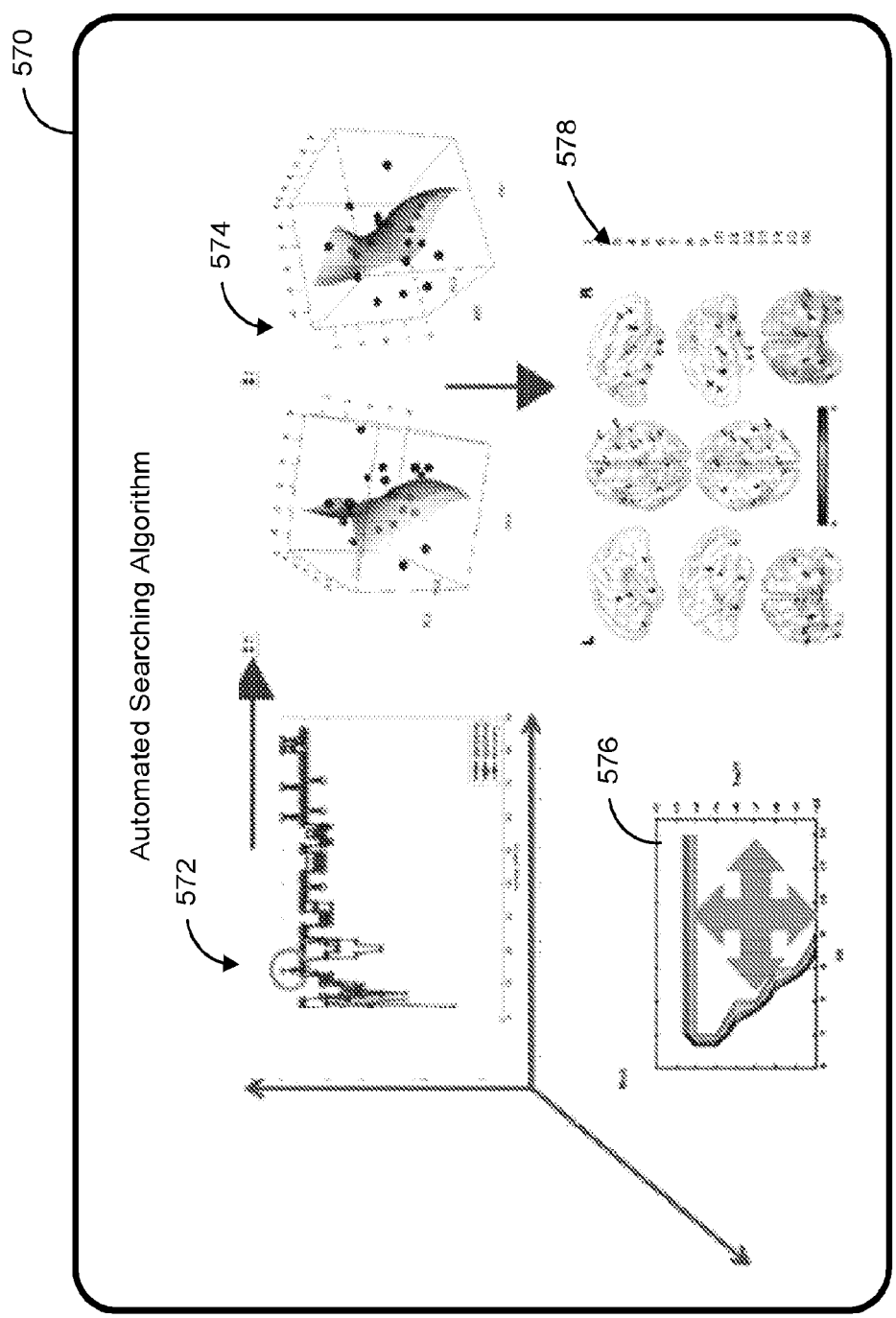

FIG. 5D is a diagram that shows one non-limiting example of an automated iterative searching algorithm utilizing a supervised nonlinear classification analysis method at the population level.

Figure 6A:
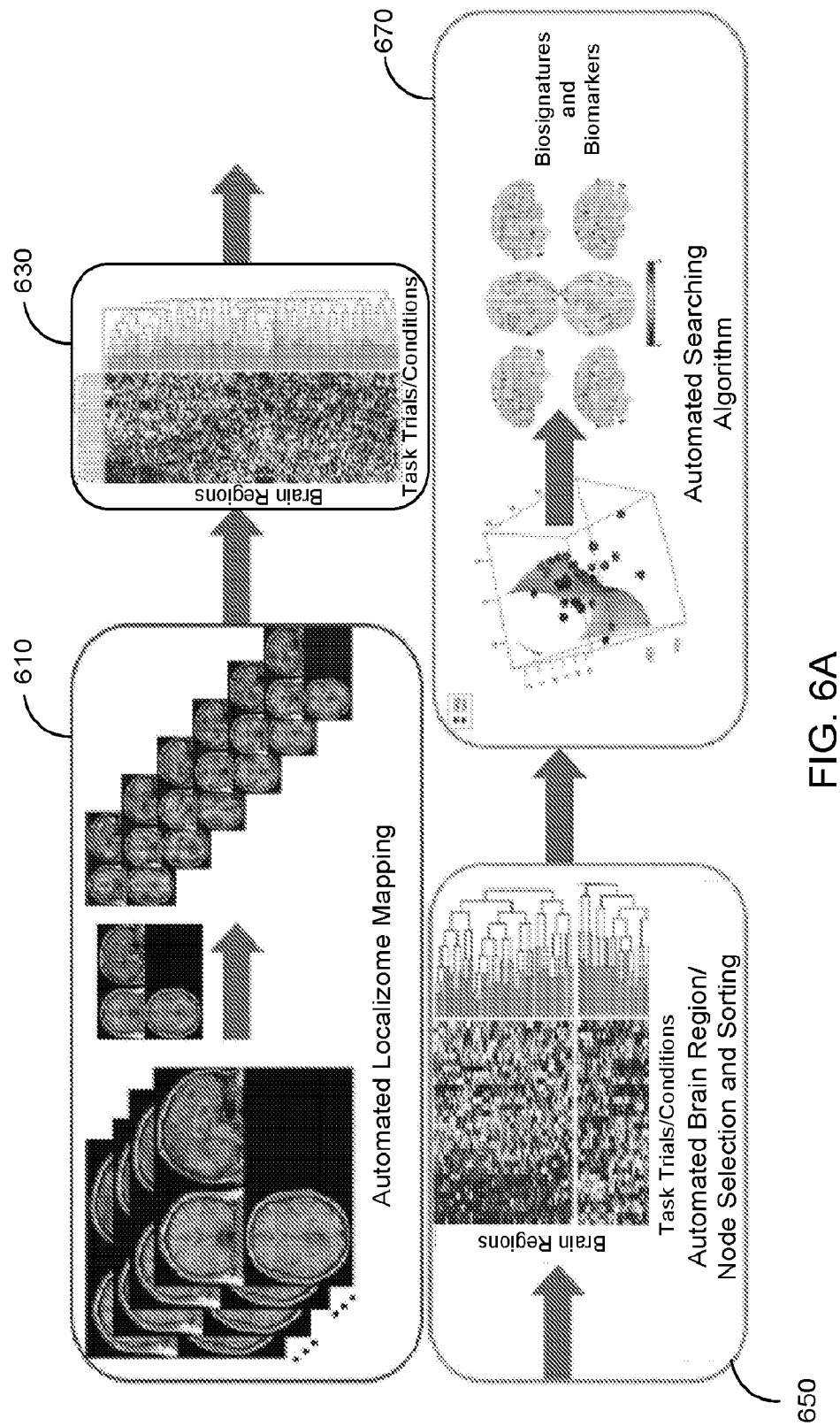

FIG. 6A is a diagram that summarizes one non-limiting example of a multivariate, automated, systematic and hierarchical searching algorithm for objective biosignature extractions for an example individual patient/subject according to the present disclosure.

Figure 6B:
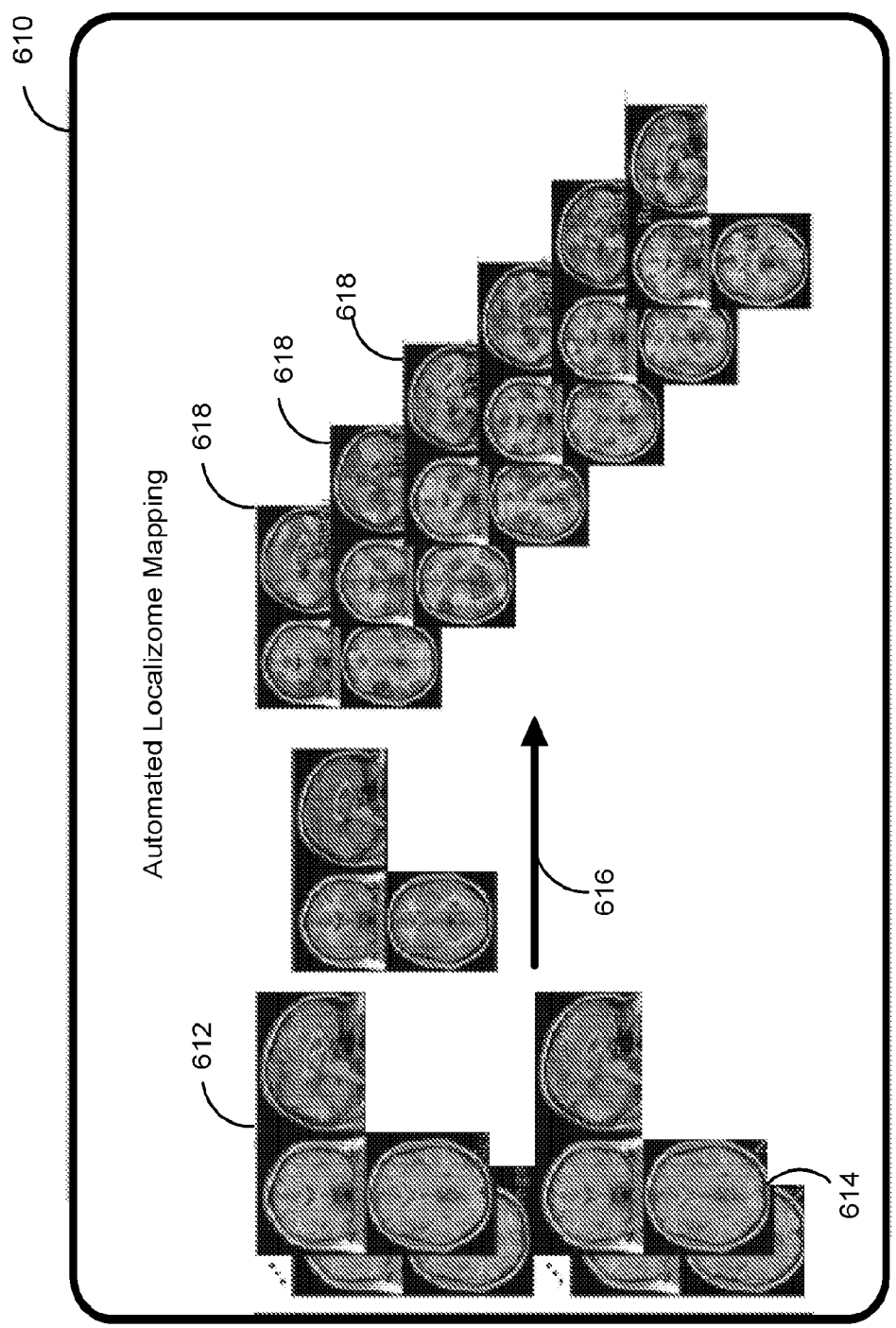

FIG. 6B is a diagram that shows one non-limiting example of an automated localizome, such as a task-condition/contrast-specific brain functional localizome, mapping algorithm based on task-based fMRI data utilizing a normalized spectral clustering method at the individual level.

Figure 6C:
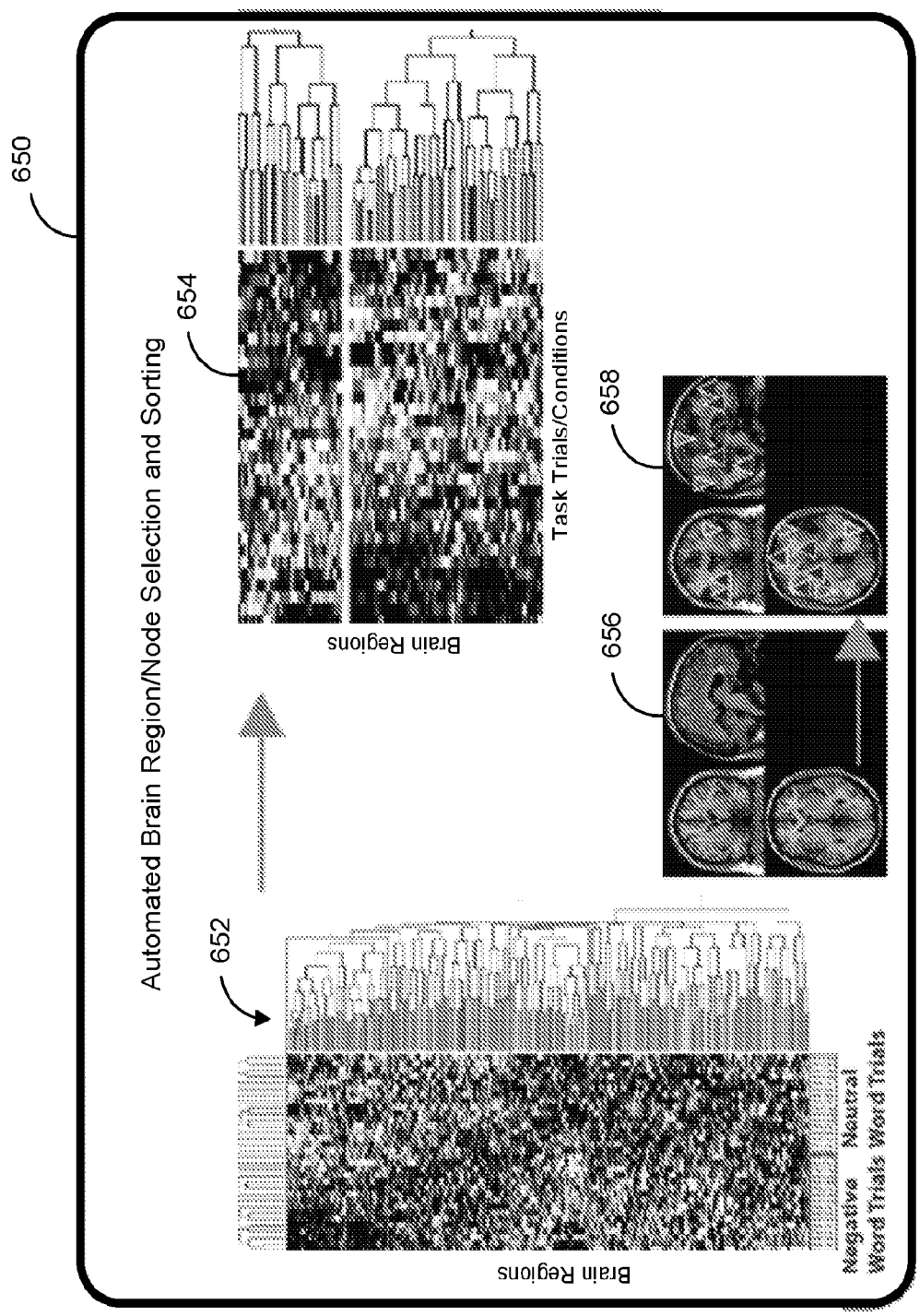

FIG. 6C is a diagram that shows one non-limiting example of an automated brain region/node selection and sorting algorithm utilizing an unsupervised two-way hierarchical clustering analysis method at the individual level.

Figure 6D:
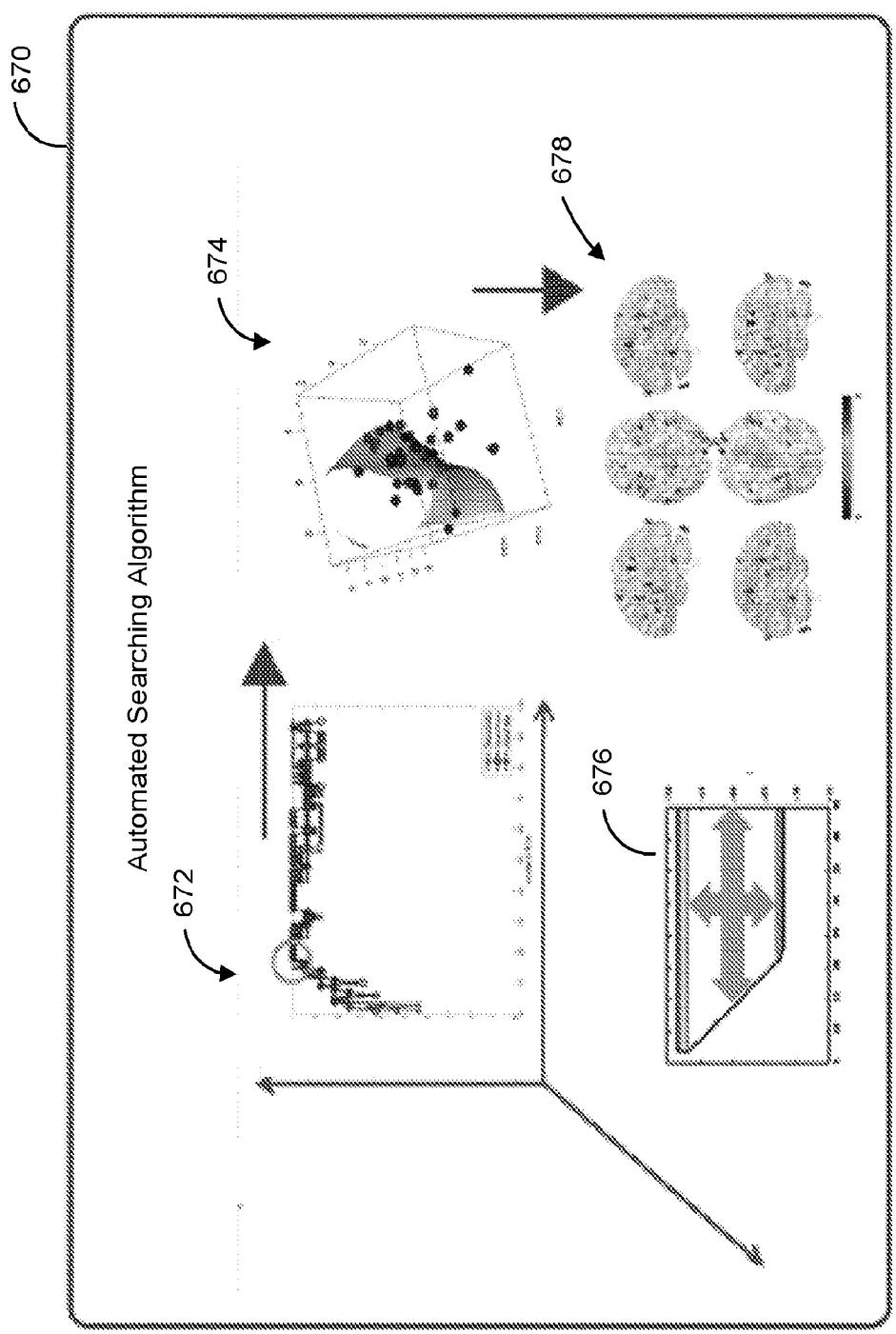

FIG. 6D is a diagram that shows one non-limiting example of an automated iterative searching algorithm utilizing a supervised nonlinear classification analysis method at the individual level.

Figure 7:
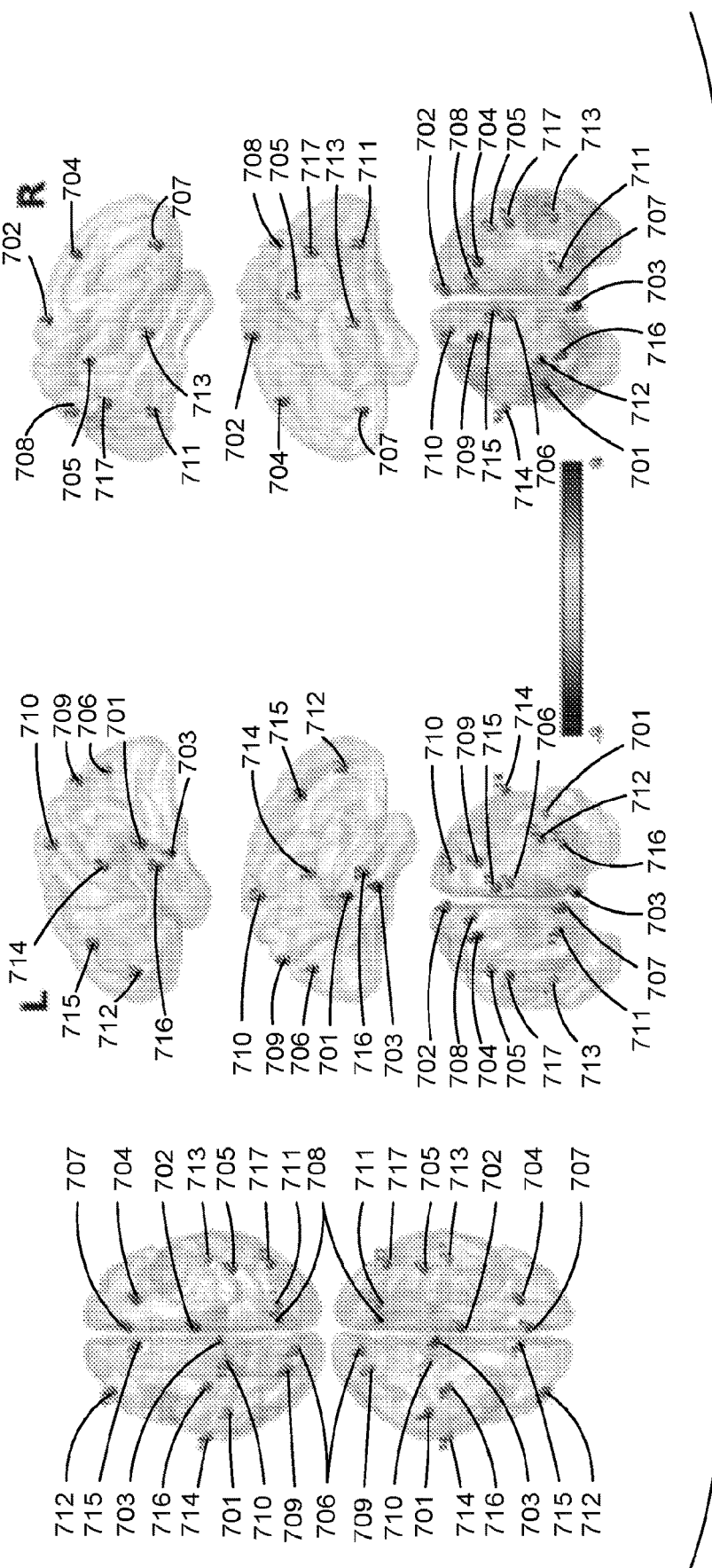

FIG. 7 illustrates one non-limiting example set of brain region biosignatures at a population level.

Figure 8:
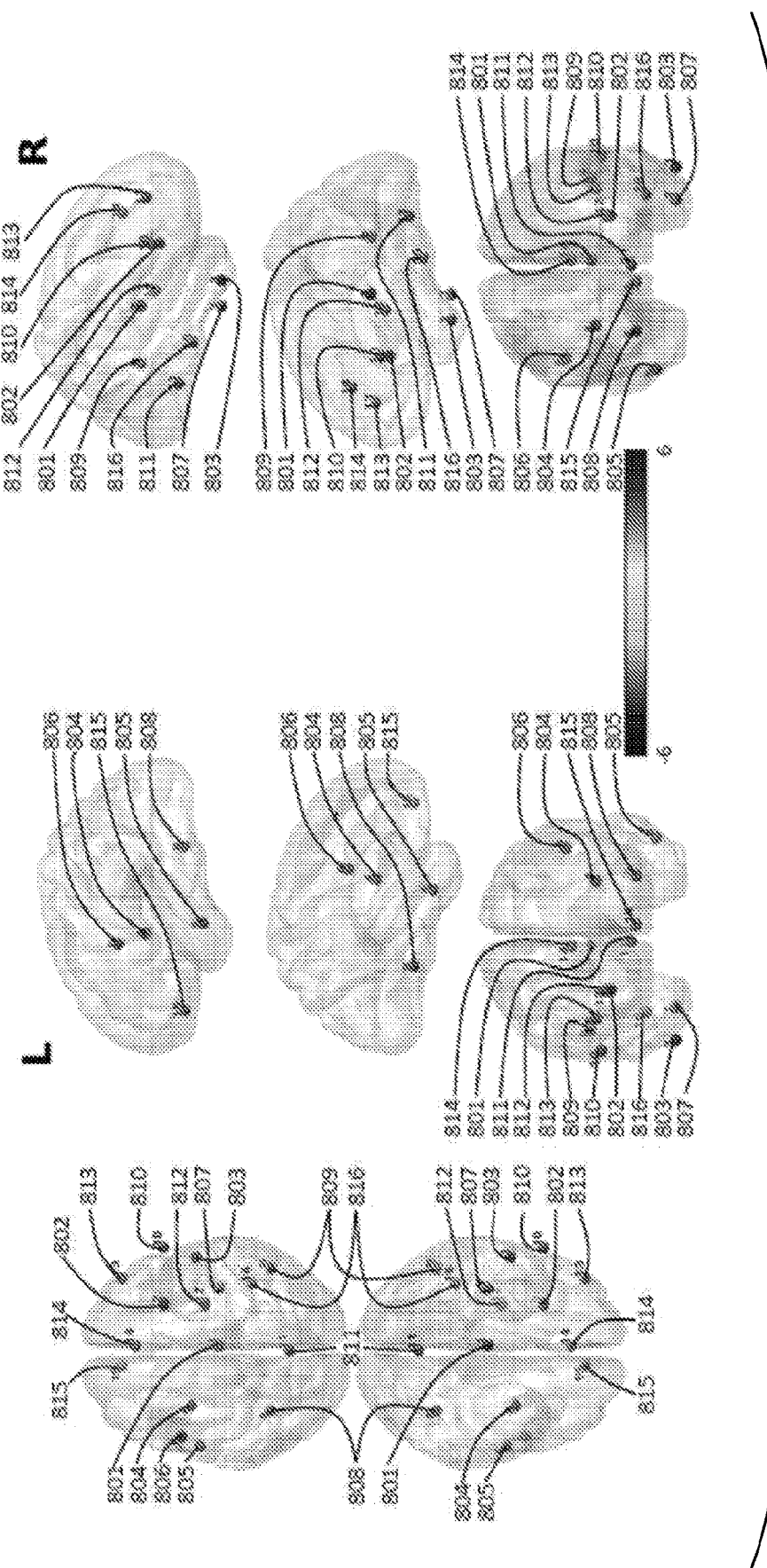

FIG. 8 illustrates another non-limiting example set of brain region biosignatures at a population level.

Figure 9:
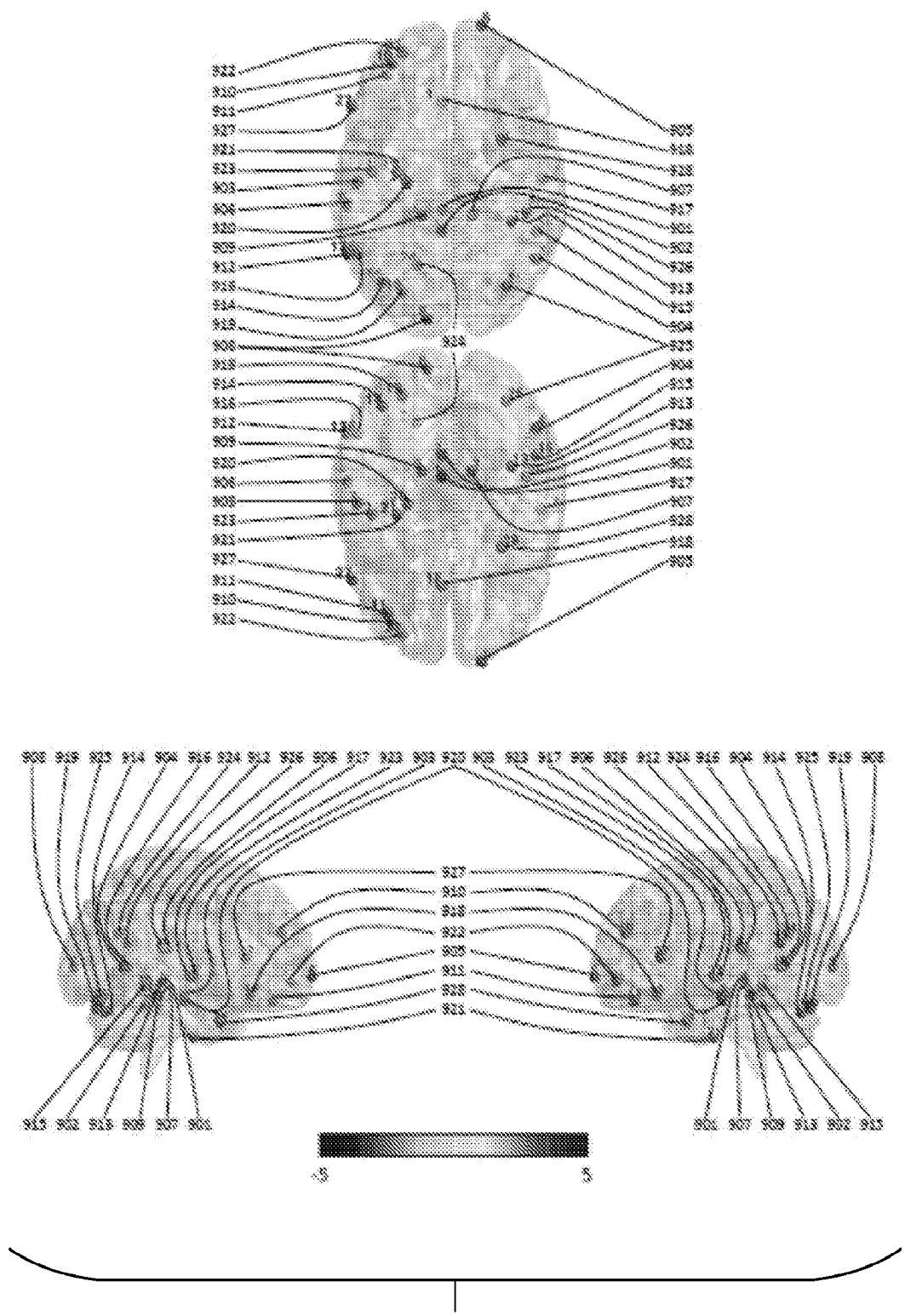

FIG. 9 illustrates yet another non-limiting example set of brain region biosignatures at a population level.

Figure 10:
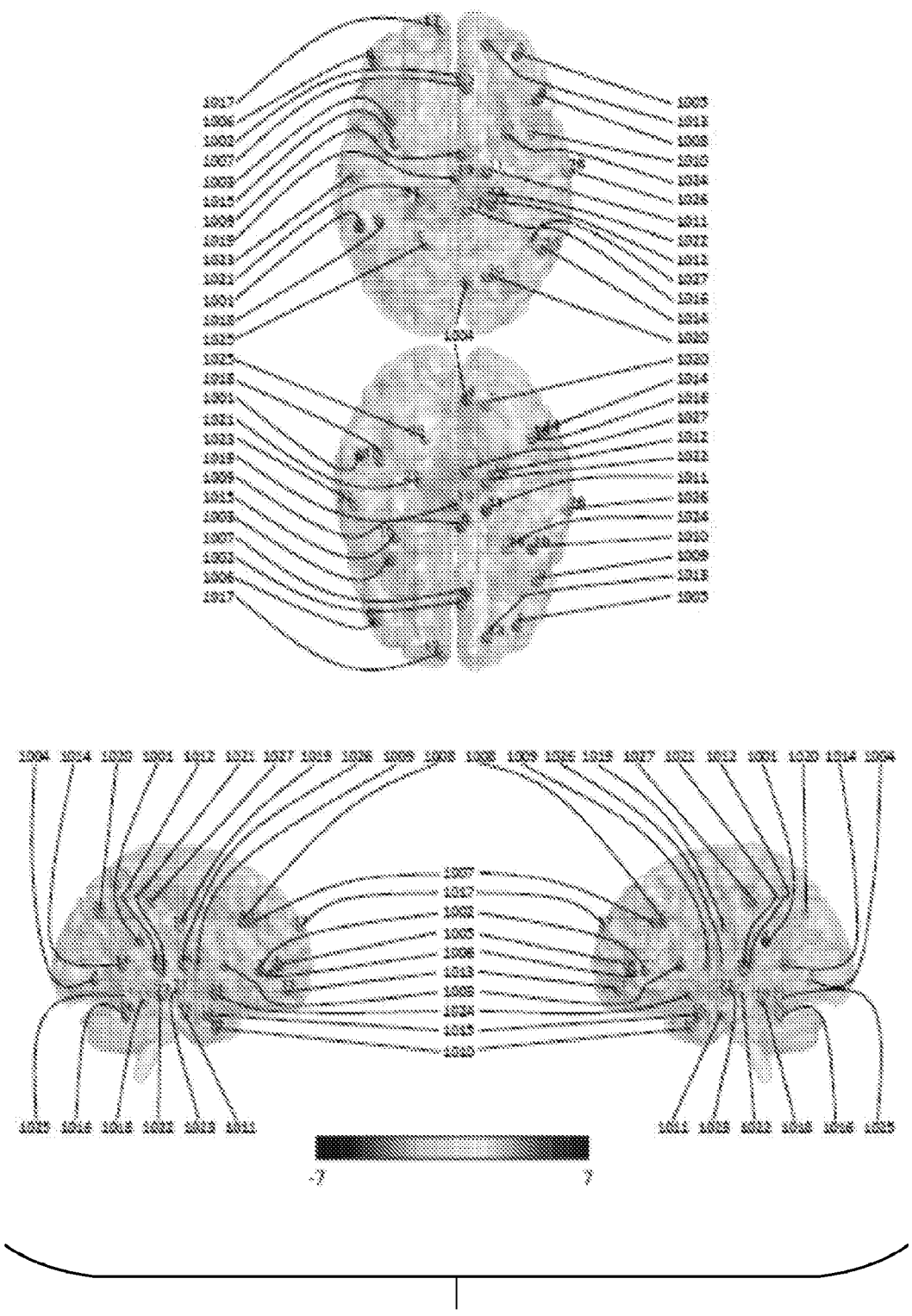

FIG. 10 illustrates still another non-limiting example set of brain region biosignatures at a population level.

Figure 11A:
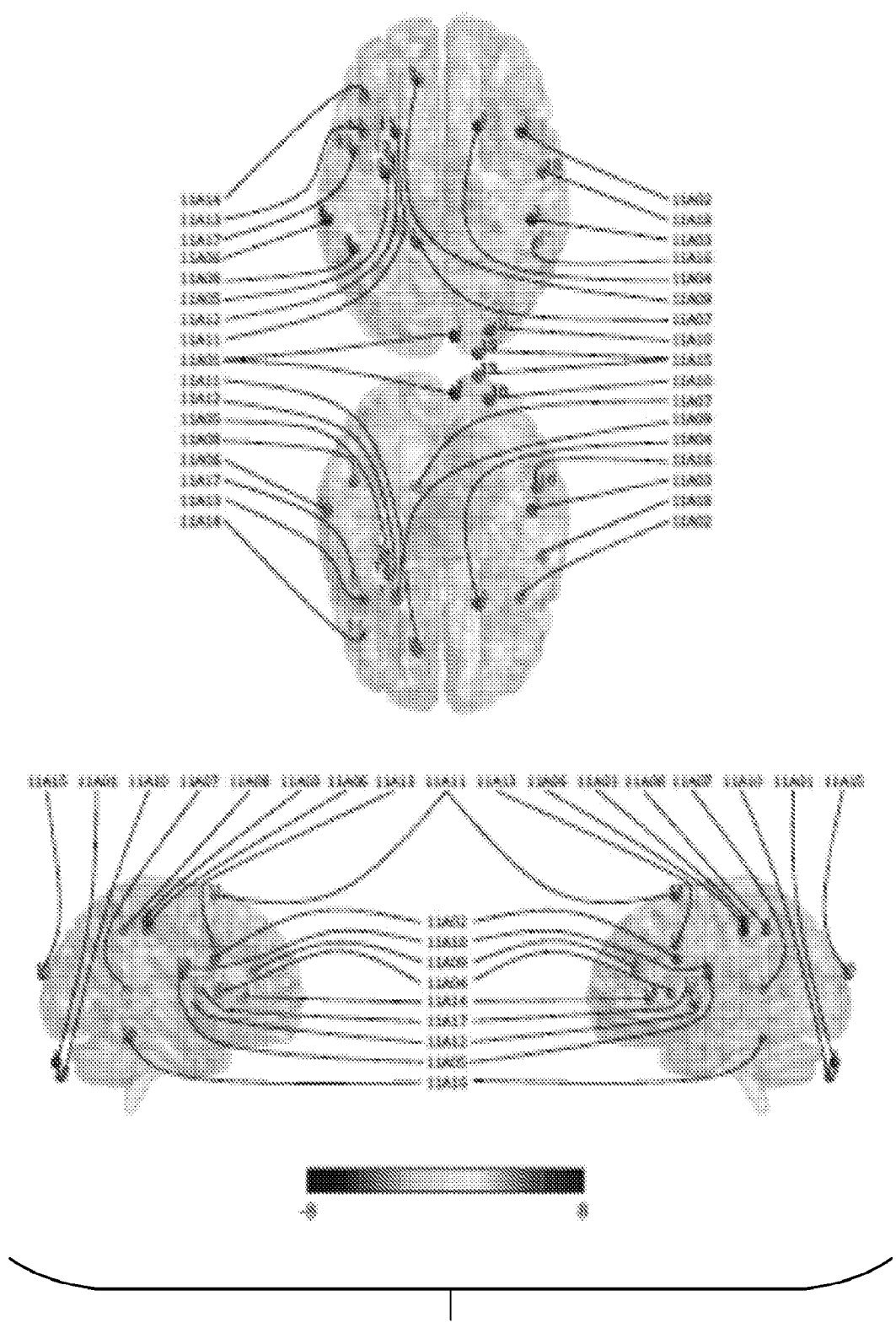

FIG. 11A illustrates yet another non-limiting example set of brain region biosignatures at an individual level.

Figure 11B:
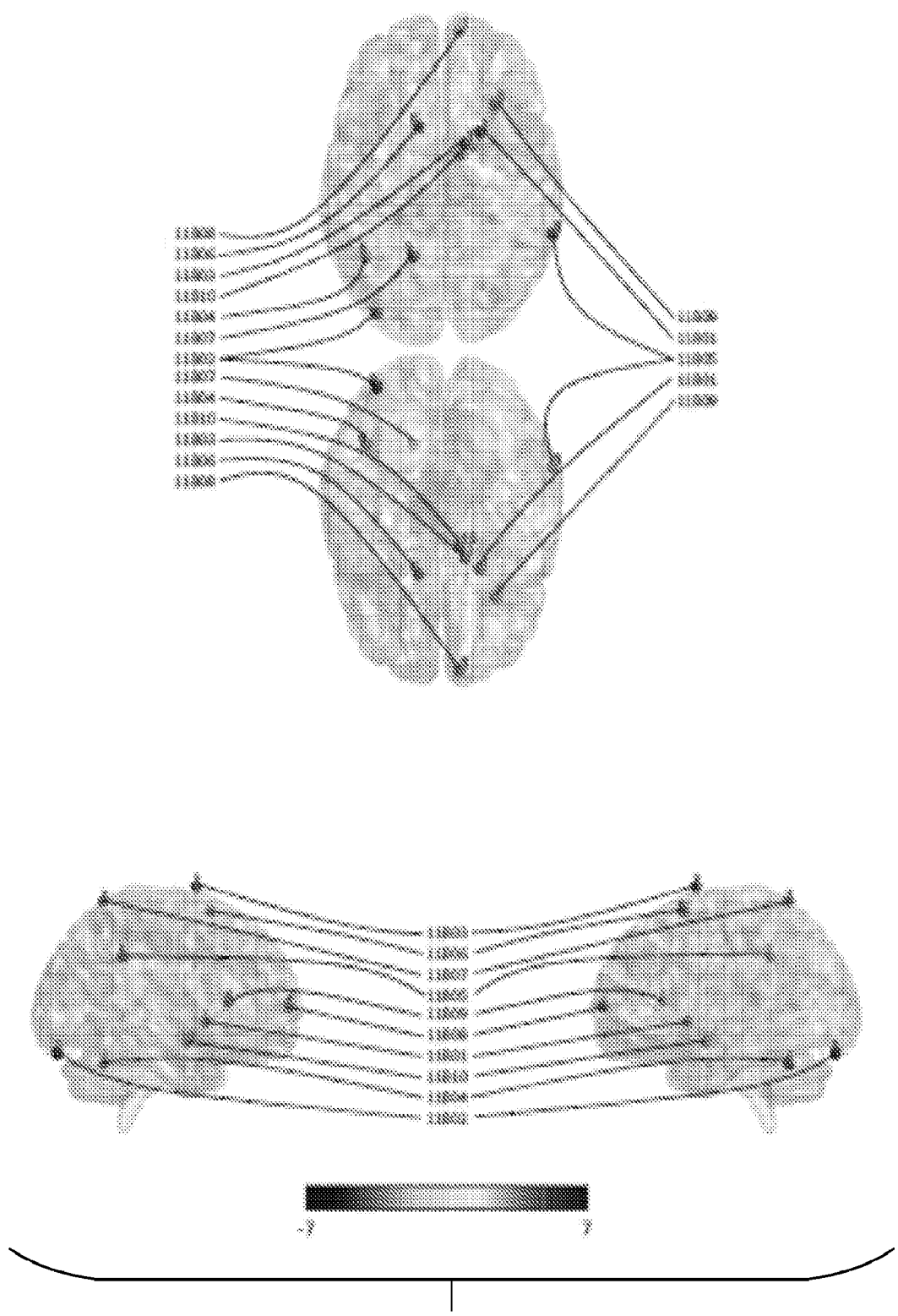

FIG. 11B illustrates another non-limiting example set of brain region biosignatures at an individual level.

DETAILED DESCRIPTION

An automated system and method is provided enabling objective biosignature extraction and biomarker discovery from task-based fMRI imaging data, to reveal hidden, implicit, and latent brain circuit patterns provoked by fMRI tasks.

The present disclosure recognizes that the amount of information that results from task-based studies makes it a powerful tool that can be used to identify objective biosignatures and neurobiological-mechanism-based biomarkers. However, the technology is made more powerful by combining image acquisition with advanced analytic techniques/bioinformatics that can automatically quantify, categorize, and summarize the results. This may be more important as the results of each study produce more relevant information than can be interpreted by the user. In order to develop a tool that can maximize the extraction of all relevant information, new methods are provided that can (1) automatically interrogate the data, identifying the most relevant functional results (removing redundancies in both space and time), and (2) automatically distill the results so the complete functional brain states resulting from the task-based perturbation can be interpreted by an end-user in a way that can guide diagnosis, treatment, prediction of outcome and the like.

To automate the whole process of imaging data interrogation in a fashion that simultaneously yields both (1) the detection of differential brain regions/nodes, (2) the detection of circuit-wise co-activation/co-varying brain regions/nodes, among patient populations and normal controls and/or among the stimulus types/conditions/contrasts, a multivariate, automated, systematic and hierarchical searching algorithm (MASHA) is provided.

In some configurations, MASHA may provide objective biosignature extraction and biomarker discovery from task-based fMRI imaging data. With this functional objective in mind, MAHSA may facilitate:

(1) Objective biosignature extractions for each individual patient/normal control subject. Within each patient or normal control subject and between/among task-based mental conditions/trials, to identify simultaneously both the greatest differential brain regions/nodes and the circuit-wise co-activation/co-varying brain regions/nodes in interacting functional subnetworks/circuits.

(2) Objective biosignature extractions within/between/among 1 or 2 or more than 2 populations of mental disorders and/or normal controls. Within each task-based condition/contrast and between/among/across populations of patients and healthy controls; to identify simultaneously both the greatest differential brain regions/nodes and the circuit-wise co-activation/co-varying brain regions/nodes in interacting functional subnetworks/circuits.

In some configurations, the system and method may present an objective and automated biosignature extraction and biomarker discovery procedure from task-based fMRI imaging data associated with neuropsychiatric disorders and their treatment with specific cognitive-behavioral, pharmacologic or brain stimulation approaches. The data may be spacetime data, or a time-series of images. These biosignatures and biomarkers that reveal hidden, implicit and latent brain circuit patterns provoked by fMRI tasks, can provide a foundation for the development of non-invasive diagnostics and targeted therapeutics in neuropsychiatric diseases.

Figure 1:
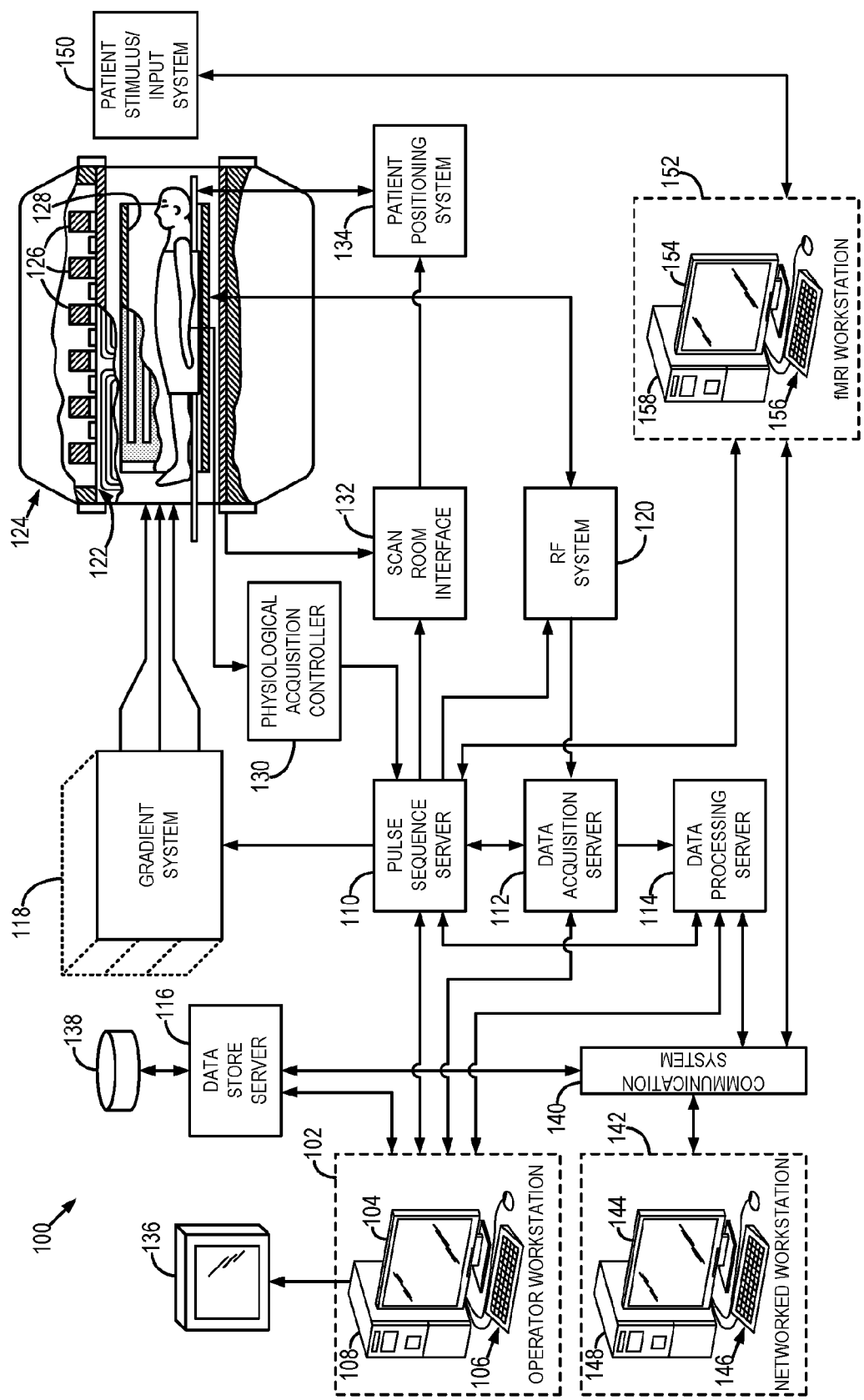
FIG. 1 is a block diagram of an example magnetic resonance imaging ("MRI") system configured with respect to systems and methods in accordance with the disclosure.

Referring particularly to FIG. 1, an example of a magnetic resonance imaging (MRI) system 100 capable of implementing the methods described above. The MRI system 100 includes a workstation 102 having a display 104 and a keyboard 106. The workstation 102 includes a processor 108 that is commercially available to run a commercially-available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116.

The MRI system 100 also includes an fMRI workstation 152 that is coupled to a patient stimulus/input system 150. The fMRI workstation 152 includes a display 154 and a keyboard 156. The fMRI workstation 152 includes a processor 158 configured with necessary hardware and software for providing the necessary patient stimuli and inputs described elsewhere herein. The fMRI workstation 152 is coupled to the pulse sequence server 110 and the communication system 140, though it is also contemplated that the fMRI workstation 152 is coupled to other components of the MRI system 100, as necessary to achieve the methods described above.

The patient stimulus/input system 150 can function in response to instructions downloaded from the fMRI workstation 152 to provide a stimulus to a subject during or prior to imaging. Stimuli may include auditory inputs, visual inputs, or decision-based tasks. The patient stimulus/input system 150 can also function to receive inputs from the subject during or prior to imaging. The patient stimulus/input system 150 can include LCD goggles or other visual displays, joysticks or other user inputs, and other stimuli-producing systems and inputs as would be understood by those having ordinary skill in the art.

The pulse sequence server 110 functions in response to instructions downloaded from the workstation 102 to operate a gradient system 118 and a radiofrequency (RF) system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128 (or a head (and neck) RF coil for brain imaging).

RF excitation waveforms are applied to the RF coil 128, or a separate local coil, such as a head coil, by the RF system 120 to perform the prescribed magnetic resonance pulse sequence. Responsive MR signals detected by the RF coil 128, or a separate local coil, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF preamplifier that amplifies the MR signal received by the coil 128 to which it is connected, and a detector that detects and digitizes the quadrature components of the received MR signal. The magnitude of the received MR signal may thus be determined at any sampled point by the square root of the sum of the squares of the I and Q components:

$$M = \sqrt{I^2 + Q^2} \qquad (1);$$

and the phase of the received MR signal may also be determined:

$$\varphi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network or communication system 140 to other facilities that may include other networked workstations 142.

The communications system 140 and networked workstation 142 may represent any of the variety of local and remote computer systems that may be included within a given clinical or research facility including the system 100 or other, remote location that can communicate with the system 100. In this regard, the networked workstation 142 may be functionally and capably similar or equivalent to the operator workstation 102, despite being located remotely and communicating over the communication system 140. As such, the networked workstation 142 may have a display 144 and a keyboard 146. The networked workstation 142 includes a processor 148 that is commercially available to run a commercially-available operating system. The networked workstation 142 may be able to provide the operator interface that enables scan prescriptions to be entered into the MRI system 100.

Figure 2:
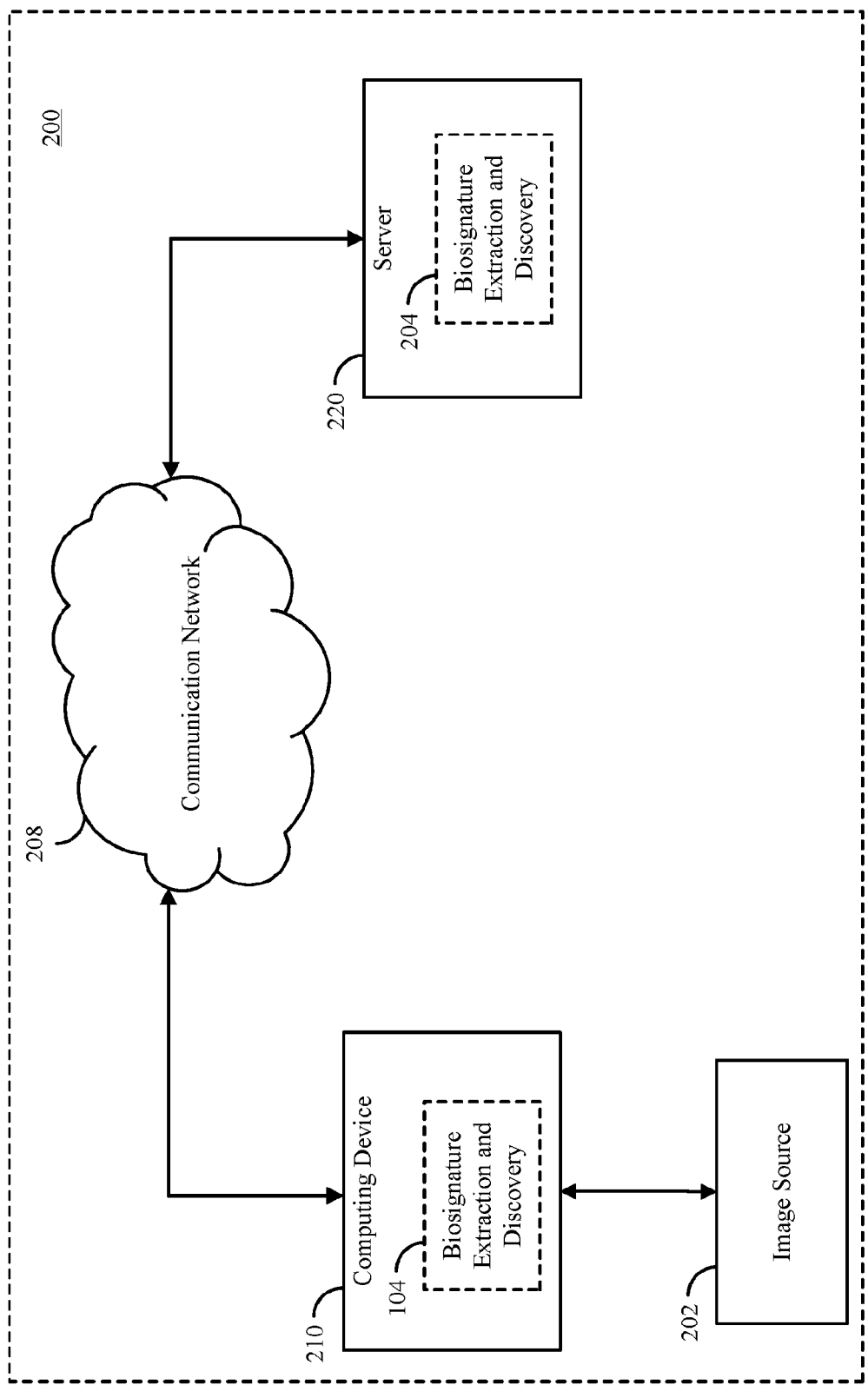
FIG. 2 is a schematic diagram of one system in accordance with the present disclosure.

Referring to FIG. 2, an example of a system 200 is shown for biosignature extraction and discovery using image data in accordance with some aspects of the disclosed subject matter. The system of FIG. 2 may be integrated with or utilize components of the MRI system 100 described with respect to FIG. 1. As shown in FIG. 2, a computing device 210 can receive multiple types of image data from an image source 202. In some configurations, the computing device 210 can execute at least a portion of an automated biosignature extraction and discovery system 204 to automatically determine whether a biosignature is present in image data of a subject.

Additionally or alternatively, in some configurations, the computing device 210 can communicate information about image data received from the image source 202 to a server 220 over a communication network 208, which can execute at least a portion of the automatic biosignature extraction and discovery system 204 to automatically determine whether a biosignature is present in image data of a subject. In such configurations, the server 220 can return information to the computing device 210 (and/or any other suitable computing device) indicative of an output of the biosignature extraction and discovery system 204 to determine whether a biosignature is present or absent.

In some configurations, the computing device 210 and/or server 220 can be any suitable computing device or combination of devices, such as a desktop computer, a laptop computer, a smartphone, a tablet computer, a wearable computer, a server computer, a virtual machine being executed by a physical computing device, etc. In some configurations, the biosignature extraction and discovery system 204 can extract biosignatures from labeled (e.g., labeled as including a biosignature, condition or disease, or normal) image data using a convolutional neural network (CNN) trained, for example, as a general image classifier, and can perform a correlation analysis to calculate correlations between the biosignatures corresponding to the fMRI image data and a database. In some embodiments, the labeled data can be used to train a classification model, such as a support vector machine (SVM), to classify features as indicative of a disease or a condition, or as indicative of normal. In some configurations, the biosignature extraction and discovery system 204 can provide biosignatures for unlabeled image data to the trained classification model.

In some configurations, the image source 202 can be any suitable source of image data, such as an MRI (anatomical T1/T2, DWI/DTI, MRS, resting-state and task-based fMRI), CT, ultrasound, PET, SPECT, x-ray, or another computing device (e.g., a server storing image data), and the like. In some configurations, the image source 202 can be local to the computing device 210. For example, the image source 202 can be incorporated with the computing device 210 (e.g., the computing device 210 can be configured as part of a device for capturing and/or storing images). As another example, the image source 202 can be connected to the computing device 210 by a cable, a direct wireless link, or the like. Additionally or alternatively, in some configurations, the image source 202 can be located locally and/or remotely from the computing device 210, and can communicate image data to the computing device 210 (and/or server 220) via a communication network (e.g., the communication network 208).

In some configurations, the communication network 208 can be any suitable communication network or combination of communication networks. For example, the communication network 208 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some configurations, the communication network 208 can be a local area network, a wide area network, a public network (e.g., the Internet), a private or semi-private network (e.g., a corporate or university intranet), other suitable type of network, or any suitable combination of networks. Communications links shown in FIG. 2 can each be any suitable communications link or combination of communications links, such as wired links, fiber optic links, Wi-Fi links, Bluetooth links, cellular links, etc.

Figure 3:
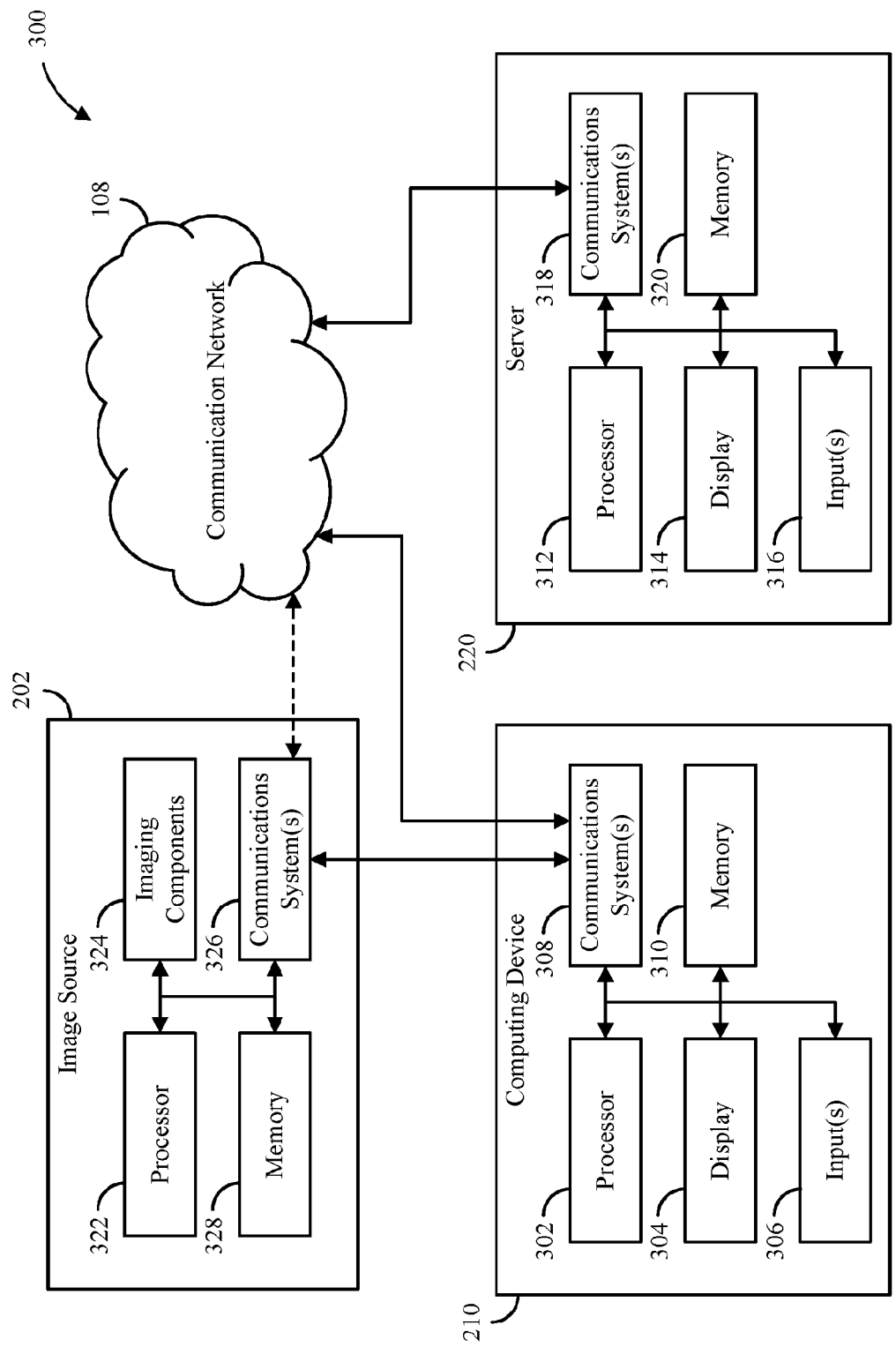
FIG. 3 is a schematic diagram showing further details of one, non-limiting example of the system of FIG. 2.

FIG. 3 shows an example of hardware 300 that can be used to implement the image source 202, computing device 210, and/or server 220 in accordance with some aspects of the disclosed subject matter. As shown in FIG. 3, in some configurations, the computing device 210 can include a processor 302, a display 304, one or more inputs 306, one or more communication systems 308, and/or memory 310. In some configurations, the processor 302 can be any suitable hardware processor or combination of processors, such as a central processing unit (CPU), a graphics processing unit (GPU), and the like. In some configurations, the display 304 can include any suitable display devices, such as a computer monitor, a touchscreen, a television, etc. In some configurations, the inputs 306 can include any of a variety of suitable input devices and/or sensors that can be used to receive user input, such as a keyboard, a mouse, a touchscreen, a microphone, and the like.

In some configurations, the communications systems 308 can include a variety of suitable hardware, firmware, and/or software for communicating information over the communication network 208 and/or any other suitable communication networks. For example, the communications systems 308 can include one or more transceivers, one or more communication chips and/or chip sets, etc. In a more particular example, the communications systems 308 can include hardware, firmware and/or software that can be used to establish a Wi-Fi connection, a Bluetooth connection, a cellular connection, an Ethernet connection, etc.

In some configurations, the memory 310 can include any suitable storage device or devices that can be used to store instructions, values, etc., that can be used, for example, by the processor 302 to present content using the display 304, to communicate with the server 220 via the communications system(s) 308, and the like. The memory 310 can include any of a variety of suitable volatile memory, non-volatile memory, storage, or any suitable combination thereof. For example, the memory 310 can include RAM, ROM, EEPROM, one or more flash drives, one or more hard disks, one or more solid state drives, one or more optical drives, etc. In some configurations, the memory 310 can have encoded thereon a computer program for controlling operation of the computing device 210. In such configurations, the processor 302 can execute at least a portion of the computer program to present content (e.g., fMRI images, user interfaces, graphics, tables, and the like), receive content from the server 220, transmit information to the server 220, and the like.

In some configurations, the server 220 can include a processor 312, a display 314, one or more inputs 316, one or more communications systems 318, and/or memory 320. In some configurations, the processor 312 can be a suitable hardware processor or combination of processors, such as a CPU, a GPU, and the like. In some configurations, the display 314 can include a suitable display devices, such as a computer monitor, a touchscreen, a television, and the like. In some configurations, the inputs 316 can include a suitable input devices and/or sensors that can be used to receive user input, such as a keyboard, a mouse, a touchscreen, a microphone, and the like.

In some configurations, the communications systems 318 can include a suitable hardware, firmware, and/or software for communicating information over the communication network 208 and/or any other suitable communication networks. For example, the communications systems 318 can include one or more transceivers, one or more communication chips and/or chip sets, and the like. In a more particular example, the communications systems 318 can include hardware, firmware and/or software that can be used to establish a Wi-Fi connection, a Bluetooth connection, a cellular connection, an Ethernet connection, and the like.

In some configurations, the memory 320 can include any suitable storage device or devices that can be used to store instructions, values, and the like, that can be used, for example, by the processor 312 to present content using the display 314, to communicate with one or more computing devices 210, and the like. The memory 320 can include any of a variety of suitable volatile memory, non-volatile memory, storage, or any suitable combination thereof. For example, the memory 320 can include RAM, ROM, EEPROM, one or more flash drives, one or more hard disks, one or more solid state drives, one or more optical drives, and the like. In some configurations, the memory 320 can have encoded thereon a server program for controlling operation of the server 220. In such configurations, the processor 312 can execute at least a portion of the server program to transmit information and/or content (e.g., fMRI data, results of automatic biosignature extraction and discovery, a user interface, and the like) to one or more computing devices 210, receive information and/or content from one or more computing devices 210, receive instructions from one or more devices (e.g., a personal computer, a laptop computer, a tablet computer, a smartphone, and the like), and the like.

In some configurations, the image source 202 can include a processor 322, imaging components 324, one or more communications systems 326, and/or memory 328. In some embodiments, processor 322 can be any suitable hardware processor or combination of processors, such as a CPU, a GPU, and the like. In some configurations, the imaging components 324 can be any suitable components to generate image data corresponding to one or more imaging modes (e.g., T1 imaging, T2 imaging, fMRI, and the like). An example of an imaging machine that can be used to implement the image source 202 can include a conventional MRI scanner (e.g., a 1.5 T scanner, a 3 T scanner), a high field MRI scanner (e.g., a 7 T scanner), an open bore MRI scanner, and the like.

Note that, although not shown, the image source 202 can include any suitable inputs and/or outputs. For example, the image source 202 can include input devices and/or sensors that can be used to receive user input, such as a keyboard, a mouse, a touchscreen, a microphone, a trackpad, a trackball, hardware buttons, software buttons, and the like. As another example, the image source 202 can include any suitable display devices, such as a computer monitor, a touchscreen, a television, etc., one or more speakers, and the like.

In some configurations, the communications systems 326 can include any suitable hardware, firmware, and/or software for communicating information to the computing device 210 (and, in some embodiments, over the communication network 208 and/or any other suitable communication networks). For example, the communications systems 326 can include one or more transceivers, one or more communication chips and/or chip sets, and the like. In a more particular example, the communications systems 326 can include hardware, firmware and/or software that can be used to establish a wired connection using any suitable port and/or communication standard (e.g., VGA, DVI video, USB, RS-232, and the like), Wi-Fi connection, a Bluetooth connection, a cellular connection, an Ethernet connection, and the like.

In some configurations, the memory 328 can include any suitable storage device or devices that can be used to store instructions, values, image data, and the like, that can be used, for example, by the processor 322 to: control the imaging components 324, and/or receive image data from the imaging components 324; generate images; present content (e.g., fMRI images, a user interface, and the like) using a display; communicate with one or more computing devices 210; and the like. The memory 328 can include any suitable volatile memory, non-volatile memory, storage, or any of a variety of other suitable combination thereof. For example, the memory 328 can include RAM, ROM, EEPROM, one or more flash drives, one or more hard disks, one or more solid state drives, one or more optical drives, and the like. In some configurations, the memory 328 can have encoded thereon a program for controlling operation of the image source 202. In such configurations, the processor 322 can execute at least a portion of the program to generate images, transmit information and/or content (e.g., fMRI image data) to one or more the computing devices 210, receive information and/or content from one or more computing devices 210, receive instructions from one or more devices (e.g., a personal computer, a laptop computer, a tablet computer, a smartphone, and the like), and the like.

Figure 4:
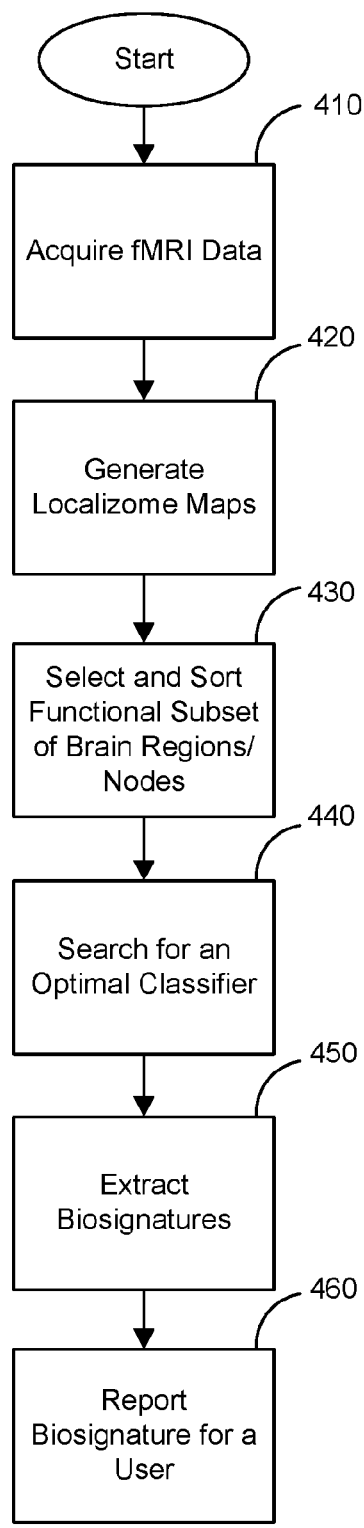
FIG. 4 is a flow chart setting forth some non-limiting example steps for a method of biosignature extraction and discovery according to the present disclosure.

Referring to FIG. 4, a flowchart is provided setting forth some non-limiting example steps for a method of biosignature extraction and discovery. fMRI data of a subject is acquired at step 410. Brain functional localizome maps may be generated at step 420 and may include summarized task-based fMRI measures, or any one or more of the following modalities of MRI images: structural/anatomical T1/T2 measures, or DWI/DTI measures, or resting-state fMRI measures, to parcellate the brain of an individual subject, or 1 or 2 or more than 2 populations of mental disorders and/or normal controls, into functionally defined brain regions or nodes for probing network connectivity endophenotypes of brain circuits. Functional subsets of brain regions or nodes may be selected and sorted at step 430. An optimal classifier based on the list of the functional subset of brain regions may be searched for, such as with an iterative search routine, at step 440. Biosignatures may then be extracted at step 450 taking into account the previous steps, and a report for a user reporting the biosignatures may be generated at step 460. A report may include a color overlay on a subject's medical image, such as an MRI T1 structural/anatomical image, where the biosignatures are discernable based upon color and location in the overlayed image. A report may also include a summary of the biosignature in text or numerical information and associated neuroinformatics for a user.

In some configurations, MASHA may include an automated brain functional localizome mapping algorithm based on task-based fMRI data, utilizing a normalized spectral clustering method: An automated, systematic brain region parcellation scheme may be based on fMRI task/condition-specific effect size images obtained from the least-biased univariate analysis methods using the multi-level mixed-effects statistical model detailed in U.S. Pat. No. 9,773,308 issued on Sep. 26, 2017, herein incorporated by reference in its entirety. In one non-limiting example, the normalized spectral clustering algorithm may be based on the graph theoretic formulation of grouping for image segmentation/partition and data clustering, using the normalized cut algorithm. In one non-limiting example, the summarized task-based fMRI measures may include: (1) At an individual patient or normal control subject level, 1 or 2 or more than 2 condition-specific, contrast between 2 or more than 2 condition-specific; (2) At the level of 1 or 2 or more than 2 populations of mental disorders and/or normal controls, 1 or 2 or more than 2 condition-specific based 1 or 2 or more than 2 populations, contrast between 2 or more than 2 condition-specific based on 1 or 2 or more than 2 populations. A set of task-condition/contrast/population-specific brain region parcellations with a pre-specified range of region numbers may then be generated using a normalized spectral clustering algorithm (which may be constrained by a searching space, such as a shared 'gray matter' mask image for a non-limiting example, defined via an algorithm that utilizes both anatomical image and functional image of each individual), to be used in the iterative searching algorithm detailed in the automated searching algorithm example below.

In some configurations, an automated brain region/node selection and sorting algorithm may be included, utilizing an unsupervised two-way hierarchical clustering analysis method, and used to select and sort the functional subset of brain regions/nodes underlying the greatest differential responses between/among the key task-conditions/contrast/populations, based on the least-biased effect size estimates extracted from the brain regions specified from the brain functional localizome mapping algorithm. The list of the functional subset of brain regions/nodes may be further sorted via a rank-sorting algorithm based on the differential effect sizes measured by t-statistic at each brain region or node between or among the key task-conditions/contrasts or populations, to be used in the iterative searching algorithm detailed below.

In some configurations, an automated searching algorithm, utilizing a supervised nonlinear classification analysis method, may be used to iteratively search for the optimal classifier based on the list of the functional subset of brain regions revealed from the automated region/node selection algorithm above. In one configuration, a leave-N-out cross-validation may be used to detect simultaneously both (i) a further narrowed list of functional brain regions underlying the greatest differential responses, and (ii) the corresponding list of functional brain regions with circuit-wise co-activation/co-varying traits with the functional brain regions found in (i), between/among the key task-conditions/contrast/populations in multi-dimensional space of functional brain regions.

In some configurations the searching algorithm may be devised to search over the following dimensions:

(a) The range of brain region parcellation (e.g., from 50 to 300 parcellation regions, with increments by 50) with iterative step sizes (e.g., from ½× median diameter of a parcellation to 3× median diameters, with increments by ¼ median diameter);

(b) The parameters for nonlinear classifier such as nonlinear SVM (a machine learning algorithm: e.g., Gamma: from $2^{-15}$ to 2 and Cost: from $2^{-5}$ to $2^{15}$, with increments $\log_2(x)$ at 2).

(c) A p-value threshold can be employed as an option to be used to prune redundant dimensions (brain regions/nodes) based on their corresponding t-statistic of contrast of interest (e.g., between-population, between-condition);

(d) A distance threshold based on the median diameter of a specific functional brain parcellation can be employed as an option to be used to spatially distinguish distinct functional regions/nodes.

The report or output of the system and method (MASHA) described above are listed below but not limited to:

(a) The set of brain regions/nodes associated with the contrast of interest (e.g., between-population, between-condition) that most differentiate functional brain states;

(b) The sets of brain regions/nodes associated with the contrast of interest (e.g., between-population, between-condition) that most co-vary/co-activate in specific functional brain states;

(c) The functionally defined brain anatomical architecture (parcellation) both at individual and population levels;

(d) The quantification of functional brain connectivity patterns including the ability to differentiate individuals and populations based upon these patterns derived from the functional brain parcellation.

Referring to FIG. 5A, a diagram that summarizes one non-limiting example of MASHA for objective biosignature extractions within/between/among 1 or 2 or more than 2 populations of mental disorders and/or normal controls according to an embodiment of the invention is shown. Automated localizome mapping, such as a task-condition/contrast/population-specific brain functional localizome, based on task-based fMRI data utilizing a normalized spectral clustering method, such as the normalized cut algorithm, is shown at step 510. A list format for the two-way hierarchical clustering analysis result with the brain regions/nodes listed in the y-axis on the left, and the individual patients and normal controls listed in the x-axis on the bottom is shown at step 530. A list of the functional subset of brain regions/nodes obtained via a rank-sorting algorithm based on the differential effect sizes in the two-way hierarchical clustering analysis result is shown at step 550. An automated searching algorithm, such as an algorithm using a supervised nonlinear classification analysis method, is shown at step 570.

Referring to FIG. 5B, a diagram for one non-limiting example of an automated localizome mapping algorithm, such as a brain functional localizome, based on task-based fMRI data utilizing a normalized spectral clustering method at the population level is shown. One configuration for step 510 from FIG. 5A is depicted in greater detail. Task-based fMRI condition-specific effect size images from individual subjects (e.g., a number of patients with DSM-5 diagnosis of Major Depression Disorder (MDD) and a number of healthy controls) are acquired at step 512. The summary effect size images of a number of task-specific conditions (e.g., one condition: when a subject is viewing neutral words during a task-based fMRI imaging session) from each subject may be used as the input images of the automated brain functional localizome mapping algorithm at step 514. A shared gray matter mask image may be defined by an algorithm that utilizes both anatomical image and functional image information of each individual to form constraints for a searching space to be used in the automated brain functional localizome mapping algorithm at step 516. A set of task-condition/contrast/population-specific brain region parcellations with a pre-specified range of region numbers (such as from 50 to 300) may be generated as the outputs of the automated brain functional localizome mapping algorithm at step 518. Any number of task-condition-specific images (e.g., from 20 patients and 20 normal controls) may be utilized as the input images to the algorithm to partition the standardized brain atlas space (e.g., the Montreal Neurologic Institute version of Talairach space) into a selected integer of parcellated regions, such as by 50 parcellations, by 100 parcellations, and the like. The resulting set of task-condition/contrast/population-specific brain region parcellations creates a searching grid of the standardized brain atlas space with incremental spatial resolutions.

Referring to FIG. 5C, is a diagram is shown for one non-limiting example of an automated brain region/node selection and sorting algorithm utilizing an unsupervised two-way hierarchical clustering analysis method at the population level. One configuration for step 550 from FIG. 5A is depicted in greater detail. The list format for the two-way hierarchical clustering analysis result with the brain regions/nodes listed in the y-axis on the left, and the individual MDD patients and healthy controls listed in the x-axis on the bottom is shown at step 552. A resulting list of candidate brain regions/nodes may span a multivariate searching space with reduced dimensionality at step 554. In some configurations, the effect sizes at each parcellated region in rendering 558 may be given a value of either 1) the condition-specific size at the peak coordinate with highest absolute t-stat between populations; or 2) the medial effect size of the parcellated region; or 3) other neuroinformatic-wise meaningful summary value for the parcellated region; or some combination thereof in image 556.

Referring to FIG. 5D, a diagram is shown for one non-limiting example of an automated iterative searching algorithm utilizing a supervised nonlinear classification analysis method at the population level. One configuration for step 570 from FIG. 5A is depicted in greater detail. Task-condition-specific effect sizes at the list of the functional subset of parcellated brain regions/nodes in step 554 of FIG. 5C, may be entered into an automated searching procedure, such as an iterative searching procedure to find an optimal classifier at step 572. A space dimension may be searched over the set of task-condition/contrast/population-specific brain region parcellations from step 518 in FIG. 5B, and a parameter dimension may be searched over SVM parameter space at step 576. Additional search options may also be available to search for the optimal classifiers with least dimensionality. The resulting list of candidate brain regions/nodes may span a multivariate searching space with reduced dimensionality at step 574, where functional brain states may be differentiated, as shown at step 578. An optimal classifier may be selected based on the classifier that most differentiates functional brain states in the most parsimonious supporting space of brain functional localizome.

Referring to FIG. 6A, a diagram is shown that summarizes one non-limiting example of MASHA for objective biosignature extractions for an example individual patient/subject according to an embodiment of the invention. Automated localizome mapping, such as a task-condition/contrast-specific brain functional localizome, based on task-based fMRI data utilizing a normalized spectral clustering method, such as the normalized cut algorithm, is shown at step 610. A list format for the two-way hierarchical clustering analysis result with the brain regions/nodes listed in the y-axis, and the condition-specific trial-wise effect size images listed in the x-axis on the bottom is shown at step 630. A list of the functional subset of brain regions/nodes obtained via a rank-sorting algorithm based on the differential effect sizes from the two-way hierarchical clustering analysis result is shown at step 650. An automated searching algorithm, such as an algorithm using a supervised nonlinear classification analysis method, is shown at step 670.

Referring to FIG. 6B, a diagram is shown for one non-limiting example of an automated localizome mapping algorithm, such as a brain functional localizome, based on task-based fMRI data utilizing a normalized spectral clustering method at the individual level. One configuration for step 610 from FIG. 6A is depicted in greater detail. Task-based fMRI condition-specific effect size images of an individual are acquired at step 612. Trial-wise effect size images of a number of task-specific conditions (e.g., two conditions: when a subject is viewing negative and neutral words during a task-based fMRI imaging session) may be used as the input images of the automated brain functional localizome mapping algorithm at step 614. A shared gray matter mask image may be defined by an algorithm that utilizes both anatomical image and functional image information of the individual to form constraints for a searching space to be used in the automated brain functional localizome mapping algorithm at step 616. A set of task-condition/contrast-specific brain region parcellations with a pre-specified range of region numbers (such as from 50 to 300) may be generated as the outputs of the automated brain functional localizome mapping algorithm at step 618. Any number of task-condition-specific images (e.g., from 16 trials of viewing negative words and 16 trials of viewing neutral words during a task-based fMRI imaging session) may be utilized as the input images to the algorithm to partition the standardized brain atlas space (e.g., the Montreal Neurologic Institute version of Talairach space) into a selected integer of parcellated regions, such as by 50 parcellations, by 100 parcellations, and the like. The resulting set of task-condition/contrast-specific brain region parcellations creates a searching grid of the standardized brain atlas space with incremental spatial resolutions.

Referring to FIG. 6C, a diagram is shown for one non-limiting example of an automated brain region/node selection and sorting algorithm utilizing an unsupervised two-way hierarchical clustering analysis method at the individual level. One configuration for step 650 from FIG. 6A is depicted in greater detail. The list format for the two-way hierarchical clustering analysis result with the brain regions/nodes listed in the y-axis on the left, and the individual trials of viewing either negative words or neutral words listed in the x-axis on the bottom is shown at step 652. A resulting list of candidate brain regions/nodes may span a multivariate searching space with reduced dimensionality at step 654. In some configurations, the effect sizes at each parcellated region in rendering 658 may be given a value of either 1) the condition-specific size at the peak coordinate with highest absolute t-stat between populations; or 2) the medial effect size of the parcellated region; or 3) other neuroinformatic-wise meaningful summary value for the parcellated region; or some combination thereof in image 656.

Referring to FIG. 6D, a diagram is shown for one non-limiting example of an automated iterative searching algorithm utilizing a supervised nonlinear classification analysis method at the individual level. One configuration for step 670 from FIG. 6A is depicted in greater detail. Task-condition-specific effect sizes at the list of the functional subset of parcellated brain regions/nodes from step 654 in FIG. 6C, may be entered into an automated searching procedure, such as an iterative searching procedure to find an optimal classifier at step 672. A space dimension may be searched over the set of task-condition/contrast-specific brain region parcellations from step 618 in FIG. 6B, and a parameter dimension may be searched over SVM parameter space at step 676. Additional search options may also be available to search for the optimal classifiers with least dimensionality. The resulting list of candidate brain regions/nodes may span a multivariate searching space with reduced dimensionality at step 674, where functional brain states may be differentiated, as shown at step 678. An optimal classifier may be selected based on the classifier that most differentiates functional brain states in the most parsimonious supporting space of brain functional localizome.

Referring to FIG. 7, one non-limiting example set of brain region biosignatures is shown which were extracted based on task-based fMRI imaging data of a population of 10 Borderline Personality Disorder (BPD) patients who went through 1-year treatment and were imaged with an fMRI paradigm using a Go-NoGo emotional word task before and after treatment intervention. The biomarkers were discovered using the MASHA system and method, via the effect size image of [Negative Word: NoGo vs Go] and contrasted in the Post-against Pre-Treatment brain state. In non-limiting examples of regions that may be labelled according to the present disclosure include: Left Middle Temperal Gyms 701, Right supplemental motor area 702, Raphe Nuclei 703, Right Superior Frontal Gyms 704, Right Parietal Eye Field 705, Left Cuneus 706, Right Ventral Medial Frontal Pole 707, Right Precuneus 708, Left Superior Parietal Gyms 709, Left Postcentral Gyms 710, Right Parahippocampal Place Area 711, Left Middle Frontal Gyms 712, Right Temporo-Parietal Junction 713, Left Postcentral Gyms 714, Left Dorsal Anterior Cingulate Gyms 715, Left Hippocampus 716, Right Angular Gyms 717.

Referring to FIG. 8, one non-limiting example set of brain region biosignatures ios shown which were extracted based on task-based fMRI imaging data between a population of 9 Major Depression Disorder (MDD) patients and a population of 11 matched healthy controls (HC) who were imaged with an fMRI paradigm using an emotional word task. The biomarkers were discovered using the MASHA system and method, via the effect size image of [Neutral Word] and contrasted in the MDD population against HC population's brain state. In non-limiting examples of regions that may be labelled according to the present disclosure include: Right Thalamus 801, Right Putamen 802, Right Inferior Temporal Gyms 803, Left Putamen 804, Left Inferior Temporal Gyms 805, Left Frontal Inferior Operculum 806, Right Fusiform Gyms 807, Left Fusiform Gyms 808, Middle Temporal Gyms 809, Right Frontal Inferior Operculum 810, Cerebellar Vermis VI 811, Right Putamen 812, Right Middle Frontal Gyms 813, Right Dorsal Anterior Cingulate Gyms 814, Left Rectus Gyms 815, Right Fusiform Gyms 816.

Referring to FIG. 9, one non-limiting example set of brain region biosignatures is shown which were extracted based on task-based fMRI imaging data between a population of 31 Schizophrenic (SZ) patients and a population of 17 matched healthy controls (HC) who were imaged with an fMRI paradigm using an emotional word task. The biomarkers were discovered using the MASHA system and method, via the effect size image of [Negative/Threat Word] and contrasted in the SZ population against HC population's brain state. In non-limiting examples of regions that may be labelled according to the present disclosure include: Superior Colliculus 901, Left Cerebellum Lobule III 902, Left Middle Temperal Gyms 903, Right Middle Temporal Visual Area 904, Right Frontal Superior Orbital Gyms 905, Wernicke's Area 906, Right Fusiform Gyms 907, Superior Occipital Gyms 908, Left Fusiform Gyms 909, Dorso-Lateral Prefrontal Cortex 910, Left Frontal Inferior Orbital Gyms 911, Left Middle Temporal Gyms 912, Right Fusiform Gyms 913, Left Cerebellum Crus I 914, Inferior Temporal Gyms 915, Left Middle Temporal Visual Area 916, Right Temporo-Parietal Junction 917, Left Ventral Medial Frontal Pole 918, Left Cerebellum Crus I 919, Left Hippocampus 920, Left Fusiform Gyms 921, Left Frontal Middle Orbital Gyms 922, Wernicke's Area 923, Left Cuneus 924, Visual Word Form Area 925, Right Temporo-Parietal Junction 926, Broca's Area 927, Temporal Pole Mid 928.

Referring to FIG. 10, one non-limiting example set of brain region biosignatures is shown which were extracted based on task-based fMRI imaging data between a population of 29 Post-Traumatic Stress Disorder (PTSD) patients and a population of 23 matched health controls (HC) who were imaged with an fMRI paradigm using an emotional word task. The biomarkers were discovered using the MASHA system and method, via the effect size image of [Negative/PTSD Word vs Neutral Word]×[Early vs Late] and contrasted in the PTSD population against HC population's brain state. In non-limiting examples of regions that may be labelled according to the present disclosure include: Wernicke's Area 1001, Right Ventral Medial Frontal Pole 1002, Left Insula 1003, Right Parahippocampal Place Area 1004, Right Middle Frontal Gyms 1005, Left Frontal Inferior Orbital Gyms 1006, Right Dorsal Anterior Cingulate Gyms 1007, Right Broca's Homolog 1008, Right Thalamus 1009, Inferior Temporal Gyms 1010, Right Entorhinal Cortex 1011, Right Hippocampus 1012, Right Frontal Superior Orbital Gyms 1013, Right Middle Temporal Visual Area 1014, Left Amygdala 1015, Right Cerebellum Crus I 1016, Left Ventral Medial Frontal Pole 1017, Left Fusiform Gyms 1018, Right Posterior Cingulate Gyms 1019, Right Superior Occipital Gyms 1020, Left Thalamus 1021, Right Parahippocampal Place Area 1022, Left Middle Temporal Gyms 1023, Right Amygdala 1024, Left Cerebellum Lobule IV/V 1025, Right Temporo-Parietal Junction 1026, Posterior Cingulate Gyms 1027.

Referring to FIG. 11A, one non-limiting example set of brain region biosignatures is shown which were extracted based on task-based fMRI imaging data of a first of two individuals who were imaged with an fMRI paradigm using an emotional word task. The biomarkers were discovered using the MASHA system and method, via the effect size images of [Negative Word] and [Neutral Word] and contrasted in the [Negative Word] against [Neutral Word]'s brain state within this individual. In non-limiting examples of regions that may be labelled according to the present disclosure include: Right Cerebellum Crus II 11A01, Right Brocca's Homolog 11A02, Right Parietal Eye Field 11A03, Right Putamen 11A04, Right Insula 11A05, Left Parietal Eye Field 11A06, Left Ventral Precuneus 11A07, Left Parietal Eye Field 11A08, Left Dorsal Anterior Cingulate Gyms 11A09, Right Cerebellum Crus II 11A10, Left Middle Frontal Gyms 11A11, Left Putamen 11A12, Left Middle Frontal Gyms 11A13, Brocca's Area 11A14, Right Superior Occipital Gyms 11A15, Right Inferior Temporal Gyms 11A16, Left Rolandic Operculum 11A17, Right Postcentral Gyms 11A18.

Referring to FIG. 11B, one non-limiting example set of brain region biosignatures is shown which were extracted based on task-based fMRI imaging data of a second of two individuals who were imaged with an fMRI paradigm using an emotional word task. The biomarkers were discovered using the MASHA system and method, via the effect size images of [Negative Word] and [Neutral Word] and contrasted in the [Negative Word] against [Neutral Word]'s brain state within this individual. In non-limiting examples of regions that may be labelled according to the present disclosure include: Right Putamen 11B01, Left Cerebellum Crus I 11B02, Right Superior Frontal Gyms 11B03, Left Cerebellum Crus I 11B04, Right Parietal Eye Field 11B05, Left Supplemental Motor Area 11B06, Left Precuneus 11B07, Right Ventral Medial Frontal Pole 11B08, Right Insula 11B09, Right Hippocampus 11B10.

The present invention has been described in terms of one or more preferred embodiments, and it should be appreciated that many equivalents, alternatives, variations, and modifications, aside from those expressly stated, are possible and within the scope of the invention.

We claim:

1. A computer-implemented method for extracting biosignatures for an individual subject having a given mental disorder, the method comprising:
   a) receiving, at a processor, task-based functional magnetic resonance imaging (fMRI) data for the individual subject and one or more populations;
   b) automatically mapping, using the processor, a localizome based on the fMRI data;
   c) automatically selecting and sorting brain regions or brain nodes, using the processor and the localizome to produce a functional subset of brain regions or brain nodes;
   d) automatically searching, using the processor, the functional subset of brain regions or brain nodes to produce a multivariate classifier indicating that the subject has particular brain circuit patterns associated with at least one symptom of the given mental disorder;
   e) generating a report indicating that the subject has a biotype associated with the given mental disorder.

2. The computer-implemented method of claim 1, wherein the localizome is a task-specific brain functional localizome; and wherein the automatically mapping includes using an automated, systematic brain region parcellation scheme.

3. The computer-implement method of claim 2, wherein the automated, systemic brain region parcellation scheme includes:
   obtaining, using the processor and the fMRI data, task- or condition-specific effect size images from a least-biased univariate analysis method using a multi-level mixed-effects statistical model;
   generating, using the processor and the task-or condition-specific effect size images, a set of task-condition-specific brain region parcellations with a pre-specified range of region numbers using a normalized spectral clustering algorithm.

4. The computer-implemented method of claim 3, wherein the normalized spectral clustering algorithm is constrained by a searching space or a shared mask image defined by an algorithm that utilized an anatomical image and a functional image of the individual subject within the one or more populations.

5. The computer-implemented method of claim 1, wherein the automatically selecting and sorting brain regions or brain nodes includes performing an unsupervised two-way hierarchical clustering analysis.

6. The computer-implemented method of claim 1, wherein the automatically selecting and sorting brain regions or brain nodes includes selecting and sorting based on differential responses between or among key tasks, conditions, populations, or treatments based on the localizome.

7. The computer-implemented method of claim 1, wherein the automatically selecting and sorting brain regions or brain nodes includes sorting via a rank-sorting algorithm based on differential effect sized measured by t-statistic between and/or among key tasks, conditions, treatments or populations.

8. The computer-implemented method of claim 1, wherein the automatically searching includes iteratively searching for the multivariate classifier based on the functional subset of brain regions.

9. The computer-implemented method of claim 8, wherein iteratively searching includes performing leave-N-out cross-validation to simultaneously detect a further narrowed list of functional brain regions with a predetermined differential response and a corresponding list of functional brain regions with circuit-wise co-activation or co-varying traits.

10. The computer-implemented method of claim 9, wherein the leave-N-out cross-validation utilizes a multi-dimensional space of functional brain regions.

11. The computer-implemented method of claim 1, wherein the searching includes performing searches over one or more of the following spacetime dimensions:
    a range of brain region parcellations with iterative step sizes;
    a set of parameters for a nonlinear classifier;
    a p-value threshold;
    a distance threshold; or
    a combination thereof.

12. The computer-implemented method of claim 11, wherein the nonlinear classifier is a nonlinear support vector machine algorithm, the p-value threshold prunes redundant dimensions based on their corresponding t-statistic of contrast of interest, the distance threshold is based on a median diameter of a specific functional brain parcellation to spatially distinguish distinct functional regions or nodes, or a combination thereof.

13. The computer-implemented method of claim 1, wherein the multivariate classifier includes one or more of the following:
    a set of brain regions or nodes associated with a contrast of interest that most differentiates functional brain states;
    a set of brain regions or nodes associated with a contrast of interest that most co-vary and/or co-activate in a specific functional brain state;
    a functionally defined brain anatomical architecture at an individual and/or population level;
    a quantification of brain connectivity patterns; or
    a combination thereof.

14. An fMRI system comprising:
    a magnet system configured to generate a polarizing magnetic field about at least a portion of a subject arranged in the fMRI system;
    a magnetic gradient system including a plurality of magnetic gradient coils configured to apply at least one magnetic gradient field to the polarizing magnetic field;
    a radio frequency (RF) system configured to apply an RF field to the subject and to receive fMRI signals therefrom;
    a computer system programmed to:
      control the fMRI system to acquire task-based fMRI data for an individual subject having a given mental disorder;
      acquire fMRI data for one or more populations;
      map a localizome based on the fMRI data for the individual subject having the given mental disorder;
      select and sort brain regions or brain nodes using the localizome to produce a functional subset of brain regions or brain nodes of the individual subject;
      search the functional subset of brain regions or brain nodes to produce a multivariate classifier indicating that the subject has particular brain circuit patterns associated with at least one symptom of the given mental disorder or its treatment; and generate a report indicating that the subject has a given biotype associated with the given mental disorder.

15. The system of claim 14, wherein the localizome includes a task-specific brain functional localizome; and wherein the map includes using an automated, systematic brain region parcellation scheme.

16. The system of claim 15, wherein the automated, systemic brain region parcellation scheme includes:
    obtaining, using a processor and the fMRI data, task- or condition-specific effect size images from a least-biased univariate analysis method using a multi-level mixed-effects statistical model;
    generating, using the processor and the task-or condition-specific effect size images, a set of task-condition-specific brain region parcellations with a pre-specified range of region numbers using a normalized spectral clustering algorithm.

17. The system of claim 14, wherein the select and sort brain regions or brain nodes includes performing an unsupervised two-way hierarchical clustering analysis.

18. The system of claim 14, wherein the select and sort brain regions or brain nodes includes selecting and sorting based on differential responses between or among key tasks, conditions, populations or treatments, based on the localizome.

19. The system of claim 14, wherein the select and sort brain regions or brain nodes includes sorting via a ranksorting algorithm based on differential effect sized measured by t-statistic between and/or among key tasks, conditions, or populations.

20. The system of claim 14, wherein the search includes iteratively searching for the multivariate classifier based on the functional subset of brain regions.

21. The system of claim 14, wherein the search includes performing searches over one or more of the following spacetime dimensions:
    a range of brain region parcellations with iterative step sizes;
    a set of parameters for a nonlinear classifier;
    a p-value threshold;
    a distance threshold; or
    a combination thereof.

22. The system of claim 14, wherein the multivariate classifier includes one or more of the following:
    a set of brain regions or nodes associated with a contrast of interest that most differentiates functional brain states;
    a set of brain regions or nodes associate with a contrast of interest that most co-vary and/or co-activate in a specific functional brain state;
    a functionally defined brain anatomical architecture at an individual and/or population level;
    a quantification of brain connectivity patterns; or
    a combination thereof.

* * * * *

UNITED STATES PATENT AND TRADEMARK OFFICE
CERTIFICATE OF CORRECTION

PATENT NO. : 11,612,322 B2
APPLICATION NO. : 16/753020
DATED : March 28, 2023
INVENTOR(S) : Emily Stern et al.

It is certified that error appears in the above-identified patent and that said Letters Patent is hereby corrected as shown below:

In the Specification

Column 1, Line 20, "ME161825" should be --MH61825--.

Column 1, Line 20, "ME158911" should be --MH58911--.

Column 15, Line 17, "Gyms" should be --Gyrus--.

Column 15, Line 19, "Gyms" should be --Gyrus--.

Column 15, Line 21, "Gyms" should be --Gyrus--.

Column 15, Line 22, "Gyms" should be --Gyrus--.

Column 15, Line 23, "Gyms" should be --Gyrus--.

Column 15, Line 24, "Gyms" should be --Gyrus--.

Column 15, Line 25, "Gyms" should be --Gyrus--.

Column 15, Line 26, "Gyms" should be --Gyrus--.

Column 15, Line 39, "Gyms 803" should be --Gyrus 803--.

Column 15, Line 39, "Temporal Gyms" should be --Temporal Gyrus--.

Column 15, Line 41, "Gyms 807" should be --Gyrus 807--.

Column 15, Line 41, "Gyms 808" should be --Gyrus 808--.

Signed and Sealed this
Twenty-third Day of May, 2023

Katherine Kelly Vidal
*Director of the United States Patent and Trademark Office*

Column 15, Line 42, "Gyms" should be --Gyrus--.

Column 15, Line 44, "Gyms 813" should be --Gyrus 813--.

Column 15, Line 44, "Gyms 814" should be --Gyrus 814--.

Column 15, Line 45, "Gyms 815" should be --Gyrus 815--.

Column 15, Line 45, "Gyms 816" should be --Gyrus 816--.

Column 15, Line 58, "Gyms" should be --Gyrus--.

Column 15, Line 59, "Gyms" should be --Gyrus--.

Column 15, Line 60, "Gyms" should be --Gyrus--.

Column 15, Line 61, "Gyms 908" should be --Gyrus 908--.

Column 15, Line 61, "Gyms 909" should be --Gyrus 909--.

Column 15, Line 63, "Gyms 911" should be --Gyrus 911--.

Column 15, Line 63, "Gyms 912" should be --Gyrus 912--.

Column 15, Line 64, "Gyms" should be --Gyrus--.

Column 15, Line 65, "Gyms" should be --Gyrus--.

Column 16, Line 1, "Gyms" should be --Gyrus--.

Column 16, Line 2, "Gyms" should be --Gyrus--.

Column 16, Line 20, "Gyms" should be --Gyrus--.

Column 16, Line 21, "Gyms" should be --Gyrus--.

Column 16, Line 22, "Gyms" should be --Gyrus--.

Column 16, Line 23, "Gyms" should be --Gyrus--.

Column 16, Line 25, "Gyms" should be --Gyrus--.

Column 16, Line 27, "Gyms" should be --Gyrus--.

Column 16, Line 28, "Gyms" should be --Gyrus--.

CERTIFICATE OF CORRECTION (continued)
U.S. Pat. No. 11,612,322 B2

Column 16, Line 29, "Gyms" should be --Gyrus--.

Column 16, Line 30, "Gyms" should be --Gyrus--.

Column 16, Line 33, "Gyms" should be --Gyrus--.

Column 16, Line 48, "Gyms" should be --Gyrus--.

Column 16, Line 50, "Gyms" should be --Gyrus--.

Column 16, Line 51, "Gyms" should be --Gyrus--.

Column 16, Line 52, "Gyms 11A15" should be --Gyrus 11A15--.

Column 16, Line 52, "Temporal Gyms" should be --Temporal Gyrus--.

Column 16, Line 54, "Gyms" should be --Gyrus--.

Column 16, Line 66, "Gyms" should be --Gyrus--.